United States Patent [19]
Wann

[11] Patent Number: 5,850,032
[45] Date of Patent: Dec. 15, 1998

[54] METHOD FOR PRODUCTION OF PLANT BIOLOGICAL PRODUCTS IN PRECOCIOUS NEOMORPHIC EMBRYOIDS

[75] Inventor: Steven R. Wann, Lawrenceville, N.J.

[73] Assignee: Union Camp Corporation, Wayne, N.J.

[21] Appl. No.: 238,018

[22] Filed: May 3, 1994

Related U.S. Application Data

[63] Continuation-in-part of Ser. No. 102,517, Aug. 5, 1993, Pat. No. 5,310,672, which is a continuation of Ser. No. 860,712, Apr. 1, 1992, abandoned.

[51] Int. Cl.$^6$ .............................. A01H 5/00; C12N 5/04
[52] U.S. Cl. .......................... 800/410; 800/123; 800/422; 800/430.1
[58] Field of Search ............................. 435/172.3, 240.4, 435/240.45, 123, 48, 410, 420, 422, 430.1; 800/DIG. 49

[56] References Cited

U.S. PATENT DOCUMENTS

| | | | |
|---|---|---|---|
| 4,615,141 | 10/1986 | Janick et al. | 47/57.6 |
| 4,672,035 | 6/1987 | Davidonis et al. | 435/240 |
| 4,886,937 | 12/1989 | Sederoff et al. | 800/1 |
| 4,924,011 | 5/1990 | Denis et al. | 549/510 |
| 4,957,866 | 9/1990 | Gupta et al. | 435/240.4 |
| 5,004,863 | 4/1991 | Umbeck | 800/205 |
| 5,019,504 | 5/1991 | Christen et al. | 435/123 |
| 5,024,944 | 6/1991 | Collins et al. | 435/172.3 |
| 5,034,326 | 7/1991 | Pullman et al. | 435/240.4 |
| 5,036,006 | 7/1991 | Sanford et al. | 435/170.1 |
| 5,036,007 | 7/1991 | Gupta et al. | 435/240.45 |
| 5,041,382 | 8/1991 | Gupta et al. | 435/240.45 |
| 5,294,549 | 3/1994 | Pullman et al. | 435/240.45 |
| 5,310,672 | 5/1994 | Wann et al. | 435/240.45 |
| 5,344,775 | 9/1994 | Smith | 435/240.48 |
| 5,407,816 | 4/1995 | Bringi et al. | 435/123 |

FOREIGN PATENT DOCUMENTS

| | | |
|---|---|---|
| 2 069 122 | 11/1993 | Canada . |
| 0 160 390 | 11/1985 | European Pat. Off. . |
| 0 256 751 | 2/1988 | European Pat. Off. . |
| 0 332 581 | 9/1989 | European Pat. Off. . |
| 0 442 175 | 8/1991 | European Pat. Off. . |
| WO 91/02071 | 2/1991 | WIPO . |
| WO 93/19585 | 10/1993 | WIPO . |

OTHER PUBLICATIONS

Sawahel, W.A., and Cove, D.J., "Gene Transfer Strategies in Plants," *Biotechnol. Adv.* 10(3): 393–412 (1992).
Attree et al., "Initiation of embryogenic callus and suspension cultures, and improved embryo regeneration from protoplasts, of white spruce (*Picea glauca*)," *Can. J. Botany* 67:1790–1795 (1989).
Becwar et al., "Somatic Embryo Development and Plant Regeneration from Embryogenic Norway Spruce Callus," *Tappi Journal* 70(4):155–160 (1987).
Bernard–Dugan, C., "Biosynthesis of lower terpenoids: Genetic and physiological controls in woody plants," in: Keathley, eds., Plenum Press, pp. 329–351 (1987).
Bolik and Koop, "Identification of embryogenic microspores of barley (*Hordeum vulgare L.*) by individual selection and culture and their potential for transformation by microinjection," *Protoplasma* 162:61–68 (1991).
Borman, S., "Scientists Mobilize to Increase Supply of Anticancer Drug Taxol," *C&EN*, pp. 11–18 (1991).
Brunold et al., "Combination of kanamycin resistance and nitrate reductase deficiency as selectable markers in one nuclear genome provides a universal somatic hybridizer in plants," *Molec. Gen.Genet.* 208:469–473 (1987).
Chaleff, R.S., "Isolation of Agronomically Useful Mutants from Plant Cell Cultures," *Science* 219:676–682 (1983).
CIEIA, "Immunoassay System For the Quantitative Detection of Taxanes in Biological Matrices," Lab. Protocol, Hawaii Biotech. Group, Inc., pp. 1–7.
Crossway et al., "Integration of foreign DNA following microinjection of tobacco mesophyll protoplasts," *Molec. Gen. Genet.* 202:179–185 (1986).
Czako and Marton, "Independent integration and seed–transmission of the $T_R$–DNA of the octopine Ti plasmid pTi Ach5 in *Nicotiana plumbaginifolia*," *Plant Mol. Biol.* 6:101–109 (1986).
Dekeyser et al., "Transient Gene Expression in Intact and Organized Rice Tissues," *The Plant Cell* 2:591–602 (1990).
Dougall et al., "Taxol 9NCS 125, 973) Production by Cell Culture," *SSIE:* Abstract 1CA 27139 2 (1979).
Durand and Harada, "Interspecific protoplast fusion in Nicotian provides evidence for a mitochondrial determinism of oligomycin–resistance," *Plant Science* 62:263–272 (1989).
Durzan and Gupta, "Somatic Embryogenesis and Polyembryogenesis in Douglas Fir Cell Suspension Cultures," *Plant Science* 52:229–235 (1987).
Edgington, S.M., "Taxol out of the woods," *Bio/Technology* 9:933–938 (1991).
Ellis et al., "Transformation of *Picea glauca* (White Spruce) by Electrical Discharge Particle Acceleration," *Appl. of Biotech. to Tree Culture, Protection and Utilization*:Abstract, Delaware, OH, Aug. 5–8, (1991.
Ellis et al., "Transient and long–term expression kinetics of β–glucuronidase in somatic vs. zygotic embryos of White spruce," *Intl. Society for Plant Molec. Biology*, Abstract 420, R.B. Hallick, ed., Tucson, AZ, Oct. 6–11, (1991).
Feirer, R.P., "Biochemical and Ultrastructural Studies of Somatic Embryogenesis of Carrot (*Daucas carota*) Inbreds," Dissertation Abstract, UMI Publ., Ann Arbor, MI (1988).

*Primary Examiner*—Elizabeth F. McElwain
*Attorney, Agent, or Firm*—Dechert Price & Rhoads

[57] ABSTRACT

The present invention relates to making precocious neomorphic embryoids (PNE) and their use for producing biological products. Specifically, the invention provides a method for increasing taxol production from embryogenic Taxus cultures by making precocious neomorphic embryoids.

The invention further provides methods of inducing somatic embryogenesis in tissue cultures derived from varieties of Taxus. In addition, the present invention provides methods of obtaining taxol, or precursors thereof, using in vitro propagated somatic embryo tissues.

8 Claims, 9 Drawing Sheets

Feirer et al., "The occurrence of Proplastids in somatic embryos of Norway spruce and carrot," *Ann. Meeting of the Amer. Soc. of Plant Physiologists* (1987).

Feirer et al., "Chloroplast ultrastructure and gene expression in embryogenic conifer callus," *IUFRO Molec. Gen. Working Group.*, Chalk River, Ontario, pp. 89–95 (1987).

Feirer and Wann, "Preliminary Evidence of Transformation and Foreign Gene Expression in Sweetgum (*Liquidambar styraciflua L.*) and Loblolly Pine (*Pius taeda L.*)," *Proc. 20th Southern Forest Tree Improvement Conf.*, Charleston, SC, pp. 381–389 (1989).

Fett–Neto et al., "Cell Culture of Taxus as A Source of the Antineoplastic Drug Taxol and Related Taxanes," *Bio/Technology* 10:1572–1575 (1992).

Friedt and Brune, "Recombination Asexual Recombination in Higher Plants," *Progress in Botany* 49:192–215 (1987).

Fromm et al., "Stable transformation of maize after gene transfer by electroporation," *Nature* 319:791–793 (1986).

Gibson et al., "Initiation and growth of cell lines of *Taxus brevifolia* (Pacific Yew)," *Plant Cell Reports* 12:479–482 (1993).

Gingas and Lineberger, "Asexual embryogenesis and plant regeneration in *Quercus*," *Plant Cell, Tissue and Organ culture* 17:191–203 (1989).

Gupta and Durzan, "Biotechnology of Somatic Polyembryogenesis and Plantlet Regeneration in Loblolly pine," *Bio/Technology* 5:147–151 (1987).

Gupta and Durzan, "Shoot multiplication from mature trees of Douglas–fir (*Pseudotsuga menziesii*) and sugar pine (*Pinus lambertiana*)," *Plant Cell Reports* 4:177–179 (1985).

Hakman et al., "The development of somatic embryos in tissue cultures initiated from immature embryos of *Picea abies* (Norway spruce)," *Plant Science* 38:53–59 (1985).

Heble, M.R., "Multiple shoot cultures: A viable alternative in Vitro system for the production of known and new biologically active plant constituents," in: Primary and Secondary Metabolism in Plant Cell Cultures, Neumann et al. eds., Springer–Verlag Publ., Berlin, pp. 281–289 (1985).

Janick et al., "In vitro Production of Cacoa Seed Lipids," *J. Amer. Soc. for Hort. Sci.* 107(5) :919–922 (1982).

Jones et al., "High level expression of introduced chimaeric genes in regenerated transformed plants," *EMBO J.* 4(10) :2411–2418 (1985).

Krogstrup, P., "Embryolike structures from cotyledons and ripe embryos of Norway spruce (*Picea abies*)," *Can. J. For. Res.* 16:664–668 (1986).

Krogstrup et al., "Somatic embryogenesis in Sitka spruce (*Picea sitchensis* (Bong.) Carr.)," *Cell Reports* 7:594–597 (1988).

Kueh and Bright, "Proline accumulation in a barley mutant resistant to trans–4–hydroxy–L–proline," *Planta* 153:166–171 (1981).

Le Page–DeGivry, M., "Influence de l'acide abscissique sur le developpement des embryons de *Taxus baccata L.* cultives in vitro," *Z. Pflanzenphysiol. Bd.* 70S:406–413 (1973).

Lewis and Croteau, "Taxol Biosynthesis," *Proc.: Second Natl. Cancer Inst. Workshop on Taxol and Taxus*, Alexandria, VA, (Sep. 1992).

Lloyd and McCown, "Commercially–feasible micropropagation of mountain laurel, *Kalmia latifolia*, by use of shoot–tip culture," *Combined Proc.–Int. Plant Propagators' Soc.* 30:421–427 (1981).

Nabors et al., "Long–Duration, High–Frequency Plant Regeneration from Cereal Tissue Cultures," *Planta* 157:385–391 (1983).

Nagmani et al., "Single–Cell Orgin and Development of Somatic Embryos in *Picea abies* (L.) Karst. (Norway spruce) and P. glauca (Moench) Voss (White spruce)," *Plant Cell Reports* 6:157–159 (1987).

Neuhaus et al., "Transgenic rapeseed plants obtained by the microinjection of DNA into microspore–derived embryoids," *Theor. Appl. Genet.* 75:30–36 (1987).

Potrykus et al., "Molecular and general genetics of a hybrid foreign gene introduced into tobacco by direct gene transfer," *Molec. Gen. Genet.* 199:169–177 (1985).

Rohr et al., "Ultrastructural Changes in Haploid Embryoids of *Larix decidua* During Early Embryogenesis," *Amer. J. Botany* 76(10):1460–1467 (1989).

Shah et al., "Engineering Herbicide Tolerance in Transgenic Plants," *Science* 233:478–481 (1986).

Shewmaker et al., "Transcription of Cauliflower Mosaic Virus Integrated into Plant Genomes," *Virology* 140:281–288 (1985).

Tautorus et al., "Factors affecting transient gene expression in electroporated black spruce (*Picea marina*) and jack pine (*Pinus banksiana*) protoplasts," *Theor. Appl. Genet.* 78:531–536 (1989).

Tautorus et al., "Somatic Embryogenesis in Conifers," *Can. J. Botany* 69:1899 (1991).

Thiel, K.A., "Escagenetics Receives Second Taxol Patent," *BioWorld Today*, p. 3, Jan. 17, 1994.

Tisserat et al., "Somatic Embryogenesis in Angiosperms," *Hort. Rev.* 1:1–78 (1979).

Vidensek et al., "Taxol Content in Bark, Wood, Root, Leaf, Twig, and Seedling from Several Taxus species," *J. Natural Products* 53(6) :1609–1610 (1990).

von Arnold and Hakman, "Regulation of Somatic Embryo Development in *Picea abies* by Absicic Acid," *J. Plant Physiol.* 132:164–169 (1988).

Wang and Janick, "In vitro Production of Jojoba Liquid Wax by Zygotic and Somatic Embryos," *J. Amer. Soc. for Hort. Sci.* 111(5) :798–806 (1986).

Wani et al., "The Isolation and Structure of Taxol, a Novel Antileukemic and Antitumor Agent from *Taxus brevifolia*," *J. Amer. Chem. Soc.* 93(9) :2325–2327 (1971).

Wann et al., "Biochemical differences between embryogenic and nonembryogenic calli of conifers," *Trees* 3:173–178 (1989).

Wann et al., "Biochemical Ddifferences Between Embryogenic and Nonembryogenic Callus of *Picea abies* (L.) Karst., " *Plant Cell Reports* 6:39–42 (1987).

Wann et al., "Norway Spruce as a model system for embryogenesis in conifers," in *Proceedings–TAPPI Res. and Devel. Conf.*, Raleigh, NC, pp. 131–136 (1986.

Witherup et al., "High performance liquid chromatographic separation of Taxol and related compounds from *Taxus brevifolia*," *J. Liquid Chromatography* 12(11):2117–2132 (1989).

Yibrah and Clapham, "Transfer of a reporter gene to *Picea abies* embryos and embryogenic callus using an electric particle accelerator," *Plant Physiol.* 79 (2,part 2) :A38 Abstract 216 (1990).

| SUMMARY OF CULTRUE INITIATION FROM IMMATURE EMBRYOS OF TAXUS GENOTYPES, 1991 | | | | |
|---|---|---|---|---|
| Genotype | Origin | Collection Date | Embryos Cultured No. | Embryogenic Cultures No. (%) |
| *T. brevifolia* | Special Trees (Corvallis, OR) | July 10 | 55 | 14(25) |
| *T. baccata* | Longwood Gardens (Kennett Square, PA) | August 10 | 10 | 3(30) |
| *T. x media* cv. "Hicksii" | " | " | 8 | 3(38) |
| *T. cuspidata* cv. "Thayerae" | " | " | 9 | 3(33) |
| *T. baccata* cv. "rependens" | " | August 28 | 34 | 5(15) |
| *T. x media* | U.S. Nat'l Arboretum (Washington, D.C.) | September 16 | 8 | 3(38) |
| *T. x media* cv. "Flushing" | " | " | 12 | 4(33) |
| *T. x media* cv. "Hicksii" | " | " | 12 | 4(33) |
| *T. cuspidata* cv. "Thompson" | " | " | 4 | 0 |
| *T. cuspidata* | " | " | 8 | 1(13) |
| TOTAL EMBRYOGENIC LINES =40 | | | | |

FIG. 3

METHOD FOR PRODUCTION OF PLANT BIOLOGICAL PRODUCTS IN PRECOCIOUS NEOMORPHIC EMBRYOIDS

This is a continuation-in-part (CIP) application of the allowed U.S. patent application Ser. No. 08/102,517, filed Aug. 5, 1993, now U.S. Pat. No. 5,310,672 which is a file wrapper continuation (FWC) of the abandoned U.S. patent application, Ser. No. 07/860,712, filed Apr. 1, 1992. Each of the above-noted U.S. patent applications are herein incorporated by reference. Applicants claim priority under 35 U.S.C. § 120, based on the chain of the applications cited above.

FIELD OF THE INVENTION

The invention is in the field of plant cell culture and pharmacology. In particular, the invention relates to the induction of somatic embryogenesis in plant tissue cultures and primary explants of the genus Taxus, specifically *T. brevifolia, T. x media*, and *T. baccata*.

The invention further relates to producing precocious neomorphic embryoids (PNE) in plants. Somatic embryos are stimulated to develop or mature in vitro, according to the present invention, and promote production of a tissue which has certain characteristics that are similar to seedlings, but unlike seedlings, are incapable of developing into a plant. This tissue is called, herein, precocious neomorphic embryoid (PNE).

The invention also relates to the surprising discovery that somatic embryos induced from explants of *T. brevifolia*, Taxus spp. produce taxane-ring containing alkaloids. Utilizing this observation, methods are described for the production of taxol and taxol precursors from in vitro propagated cultures of somatic embryos and precocious neomorphic embryoids (PNE).

The invention, more specifically, relates to increasing production of taxol in vitro by stimulating Taxus somatic embryos to develop or mature into precocious neomorphic embryoids which produce significantly higher amounts of taxanes than the Taxus somatic embryos.

BACKGROUND OF THE INVENTION

A. Precocious Germination and Precocious Neomorphic Embryoids

The principle use of somatic embryogenesis has been for plant propagation. Plant propagation via somatic embryogenesis is dependent on the successful maturation of somatic embryos and their subsequent germination into seedlings. The combined process, maturation plus germination has been termed embryo conversion. Plant propagation by somatic embryogenesis has been severely limited due to low conversion frequencies (i.e., many somatic embryos could be produced, but relatively few ultimately developed into plants). Low conversion frequencies were often traced to failure in the maturation step. In particular, somatic embryos would complete the early stages of embryo development, but would bypass or truncate the middle to late stages and attempt to germinate before the embryo was sufficiently mature. Because the middle and late stages of embryo development are so important to the ultimate survival and fitness of the plant, skipping or truncating these stages resulted in weak seedlings that rarely survived transfer ex vitro. This "precocious germination" has been extensively studied in the field of somatic embryogenesis. Interestingly, there is a naturally occurring counterpart to this process, termed vivipary.

Inasmuch as plant propagation has been the principle objective of somatic embryogenesis, and precocious germination has been a major roadblock to successful propagation, much effort was put into reducing or eliminating precocious germination. Culture conditions have been discovered that will maximize the maturation efficiency of somatic embryos by minimizing precocious germination, the most important of which in conifers like Taxus is the inclusion of abscisic acid (ABA) into the culture media (von Arnold and Hakman, *J. Plant Pysiol.* 132:164–169 (1988)).

Until now, precocious germination has been viewed as a developmental "dead end" due to the emphasis placed on somatic embryogenesis for plant propagation. Prior studies on the production of biologicals from somatic embryos have been confined to seed or embryo products such as cacao seed lipids (Janick et al., *J. Amer. Hort. Soc.* 107:919–922 (1982)) and jojoba wax (Wang and Janick, *J. Amer. Hort. Soc.* 111:798–807 (1986)) rather than compounds associated with the vegetative (i.e., non-seed) parts of the plant. In the present invention, however, the products of precocious germination (termed here PNEs) have been studied and shown to possess the ability to produce biologicals which are characteristic of the intact plant. Therefore, PNEs, although known, should be considered as an entirely new tissue type for the large-scale production of biologicals contained in the non-seed portion of the plant of interest.

B. Taxol and the Production of Secondary Plant Metabolites In Vitro

Taxol, a diterpene, was first identified in 1964 and has subsequently been shown to have anti-cancer activity against ovarian cancer, breast cancer, small-cell lung cancer, melanoma, and colon cancer.

Taxol is produced primarily in the bark and cambial tissue of the pacific yew *Taxus brevifolia*. Using current purification procedures, 1 kilogram of taxol requires processing of approximately 10,000 kilograms of bark. This is equivalent to 2,000–4,000 sixty to seventy year old trees. Recent estimates put the need of taxol at approximately 250 kilograms of the purified drug per year. This is equivalent to a yield of 25 million kilograms of dried bark or approximately 750,000 trees. Due to the shortage of the pacific Taxus, other sources of taxol are currently being sought.

One potential source of taxol which has been examined is in vitro cultured plant cells and tissues. U.S. Pat. No. 5,019,504 describes the initiation and proliferation of callus cell cultures from explants of *T. brevifolia*. The callus cells produced by this procedure were shown to produce taxol. Fett-Nato et al., (*BiolTechnology* 10:1572–1575 (1992)) describe the initiation and proliferation of callus cultures from explants of *T. cuspidata*. Callus cultures produced in this report also were shown to produce taxol.

There are several obstacles to the use of callus or undifferentiated cell cultures as a means of producing secondary metabolites such as taxol. Typically, secondary metabolites are produced by specialized or differentiated tissues; most notably bark in the case of taxol, or leaves in the case of other taxanes such as baccatin. Undifferentiated, or callus cultures often lack the necessary biosynthetic capacity to assemble molecules as complex as taxanes, or, the degree of cytodifferentiation required to sequester these molecules once synthesized. The result has been that many secondary metabolites are not found in callus cultures, and, in cases where they have been detected in callus, the concentration is usually very much lower than that in planta.

Nevertheless, callus cultures have been extensively investigated for the production of secondary metabolites due to their ease of establishment, manipulation and rapid growth rate. Often, for investigations in vitro, rapidly-growing callus cultures are the most convenient way to produce the large quantities of tissue required for detection of secondary metabolites such as taxol that are found in such low concentrations. The rapid growth rate of callus cultures underscores another of their disadvantages in that the cells that comprise these cultures tend to be genetically unstable, demonstrating high levels of genetic recombination and unstable ploidy levels. Such genetic instability can ultimately lead to cultures with diminished taxol production capacity. In order to avoid this problem, callus cultures need to continually be reestablished from a genetic stock.

For the large scale production of secondary plant products in vitro, it would be desirable to combine the rapid growth rates and capacity for high biomass concentrations of undifferentiated cell culture systems with the genetic stability and the inherent capacity for secondary metabolite production of differentiated cells or tissues. Researchers have realized the potential for secondary metabolite production in cultures that proliferate in a manner akin to undifferentiated cell cultures (i.e., callus or cell suspension), but are instead comprised of differentiated cells or tissues. For example shoot cultures (tissue cultures comprised of masses of rapidly proliferating shoots) have been investigated as sources of essential oils and alkaloids that are found in leaf or stem tissue (Heble, in: *Primary and Secondary Metabolism in Plant Cell Cultures*, Neumann et al. (ed.), Springer-Verlag, Berlin Heidelberg, pp.281–289 (1985)). In shoot cultures, the specific tissue types that produce and sequester essential leaf oils are multiplied, and the rigid developmental program required for shoot morphogenesis also minimizes genetic instability. In this way, tissue cultures have been shown to combine the attractive features of both undifferentiated and differentiated systems.

Although taxol has been detected in undifferentiated cell culture systems, its production has not been described in tissue culture systems. One such system is embryogenic tissue cultures.

Embryogenic conifer tissue cultures are strikingly dissimilar to conifer callus cultures biochemically, histologically, and in macroscopic appearance. Although the term "callus" is a generic term used to describe cell and tissue cultures, many researchers in the field of conifer somatic embryogenesis object to the use of "callus" in describing embryogenic conifer tissue (See for example Gupta and Durzan, *Bio/Tech.* 5:147–151 (1987); Rohr et al., *Amer. J. Bot.* 76:1460–1467 (1988); Tautorus et al., *Can. J. Bot.* 69:1873–1899 (1991)). The reason for the objection to the use of the term "callus" is that, rather than being comprised of undifferentiated cells, embryogenic conifer tissue cultures are comprised of differentiated cells (suspensor-like cells) and structures analogous to early stage embryos found in developing seeds. Therefore, embryogenic conifer tissue cultures do not fit the definition of callus or their liquid counterparts, cell suspension cultures, and represent an improved way to produce taxol by the embodiment of the beneficial growth characteristics of cell culture systems with the capacity for secondary metabolite production of tissue culture systems.

C. Somatic Embryogenesis in Conifers

Although procedures for the induction of somatic embryogenesis have been known in the art for some time (Tisserat et al., *Hort. Rev.* 1:1–78 (1979)), it has only been recently demonstrated successfully with coniferous species (see Hakman et al., *Plant Sci.* 38:53–59 (1985)). Since the first reports of successful induction of somatic embryogenesis in conifer cell cultures, twenty-one (21) species from the genera Pinus, Picea, Abies, Larix and Psuedotsuga (Tautorus et al., *Can. J. Bot.* 69:1873–1899 (1991)), have been demonstrated as having the capacity to produce somatic embryos.

The production of somatic embryos from conifers is not universal. Several important varieties have yet to be successfully cultured, such as members of the genus Taxus. The present invention provides such a method, as well as the use of the somatic embryos of Taxus for production of Taxane-ring containing compounds.

D. Transgenic Plants

Recent advances in recombinant DNA and genetic technologies have made it possible to introduce and express a desired gene sequence in a recipient plant. Through the use of such methods, plants have been engineered to express gene sequences that are not normally or naturally present in the native plant, or to exhibit altered expression of naturally occurring genes. Plants produced through the use of recombinant techniques are known as "transgenic" plants.

Transgenic plants are generally produced by transforming a single plant cell and then regenerating a whole plant from the cell via somatic embryogenesis or organogenesis. Since many genera of plants have been regenerated from a single cell (Friedt, W. et al., *Prog. Botany* 49:192–215 (1987); Brunold, C. et al., *Molec. Gen. Genet.* 208:469–473 (1987); Durand, J. et al., *Plant Sci.* 62:263–272 (1989); Attree et al., *Can. J. Bot.* 67:1790–1795 (1989)), successful production of transgenic plants from a wide variety of plant groups is theoretically possible.

Several methods have been developed to deliver and express a foreign gene into a plant cell. These include engineered Ti plasmids from the soil bacterium *A. tumeaciens* (Czako, M. et al., *Plant Mol. Biol.* 6:101–109 (1986); Feirer et al., *Proceedings 20th Southern Forest Tree Improvement Conference*, Jun. 26–30, 1989, Charleston, S.C., pg. 381; Jones, J. D. G. et al., *EMBO J.* 4:2411–2418 (1985), engineered plant viruses such as the cauliflower mosaic virus (Shah, D. M. et al., *Science* 233:478–481 (1986)); Shewmaker, C. K. et al., *Virol.* 140:281–288 (1985)), microinjection of gene sequences into a plant cell (Crossway, A. et al., *Molec. Gen. Genet.* 202:179–185 (1986); Potrykus, I. et al., *Molec. Gen. Genet.* 199:169–177 (1985)), electroporation (Fromm, M. E. et al., *Nature* 319:791–793 (1986); Tautorus et al., *Theor. Appl. Genet.* 78:531–536 (1989), and DNA coated particle acceleration (Bolik, M. et al., *Protoplasma* 162:61–68 (1991)). Several of these procedures have been successfully employed to transform conifer tissues in vitro. (Ellis et al., *International Society of Plant Molecular Biology*, meeting of Oct. 6–11, 1991, Tucson, Ariz.).

SUMMARY OF THE INVENTION

In the present invention, PNEs have been studied and characterized for their capability to produce secondary metabolites and other biologicals in sufficiently high amounts so as to be regarded as a valuable source of desirable biological products. "Biologicals" or "biological products" as used in the present specification describe compounds or metabolites which are produced and accumulated in plants. "Metabolites" as used in the present specification refer to compounds produced in a cell as a product of metabolism, not including products ubiquitous to all plant types such as structural proteins.

More specifically, the use of PNEs for the production of taxane ring-containing compounds and related compounds is described herein, and a procedure describing their production is taught in sufficient detail such that anyone skilled in the art could produce PNEs in any species without undue experimentation. PNEs may be produced from any seed-producing vascular plant, including gymnosperms and angiosperms, which in turn encompass all monocots and dicots. In addition, an understanding of the present disclosure, enables the skilled artisans to determine a priori the type and concentration of the biologicals that PNEs can produce in a given species of vascular plant.

Somatic embryogenesis is the process by which somatic cells (i.e., non-sex cells) develop into entire plants through a series of stages characteristic of zygotic embryo development. Accordingly, somatic embryogenesis has been employed by many as a means of plant propagation. Because somatic embryo development so faithfully mirrors the same process in seed, somatic embryogenesis forms a convenient system for the study of plant embryology. This has included the study of accumulation of substances peculiar to seed, such as fats, oils and storage proteins. In this regard, it is easy to imagine the use of somatic embryos as a means of producing biologicals associated with seed as for plant propagation.

It has now been discovered that somatic embryogenesis can be used to produce substances not typically found in seed, but located in other portions of the plant (stem, roots, bark, etc.). By inducing the formation of PNEs from somatic embryos, natural products (biologicals) and/or secondary metabolites not typically associated with embryos are produced.

The later stages of embryo maturation are very important to the formation of intact plants as well as to the production of biologicals associated with seed. In PNEs, the later stages of embryo maturation are truncated or bypassed; nevertheless, germination begins. Although, mature somatic embryos or entire plants are not produced, the resultant PNEs, are comprised of tissue akin to that found in seedlings or stems. This tissue can accumulate biologicals, characteristic of the intact plant, at concentrations similar to those found in planta. Therefore, the large-scale culture and extraction of PNEs (or the media used to grow them) can form the basis of a commercial production system for natural products.

PNEs offer several advantages for the production of plant biologicals when compared to production systems based on intact plants or other in vitro plant cell and tissue culture systems.

Because PNEs are tissue cultures: (1) the potential exists for rapid growth rates rivaling that of bacterial fermentation, and, (2) they are comprised of differentiated tissue such that the production of biologicals is no longer inversely proportional to growth rate as with cell culture (i.e., dedifferentiated) systems. PNEs are based on somatic embryogenesis, which is a single-cell phenomena. Because genetic transformation techniques require the ability to regenerate plants or tissues from single cells, PNEs can be genetically engineered for increased production of biologicals. As the cultivation of genetically engineered plants is subject to strict governmental regulation in some species, PNEs offer a way of growing plant tissue engineered for overproduction in vitro without having to face restrictions associated with environmental release of an engineered "chemotype".

Finally, the metabolism of PNEs can be controlled more exactly than that of intact plant tissue. Culture conditions can accentuate or attenuate biosynthetic pathways, opening up the possibility that new types of compounds closely related to the target biological but with improved properties might be produced.

The invention further relates to in vitro production of Taxane ring-containing compounds. For the production of taxol and related taxanes, embryogenic tissue cultures of conifers (i.e., Taxus) combine the attractive growth rate and biomass production capabilities of callus cultures with the capacity for secondary metabolite accumulation inherent to differentiated cells. Although taxol was detected in callus cultures of *T. brevifolia* (Christen et al., U.S. Pat. No. 5,019,504) the yield has not been reported. Recent publications by Gibson et al., (e.g., *Plant Cell Rpts.* 12:479–482 (1993)) report yields of 0.001% on a dry weight basis. Fett-Nato et al., (*Biotechnology* 10:1572–1575 (1992)) report yields of up to 0.02% in *T. cuspidata*.

The present invention is further directed to cultured Taxus embryogenic tissue. Embryogenic tissue cultures of Taxus can be handled much the same way as conventional callus cultures but have the capacity for a greater yield of taxanes as they contain tissues with the ability to produce and sequester taxanes.

Embryogenic conifer tissue is a unique tissue type even to the field of somatic embryogenesis, and the potential of this material in plant propagation and secondary metabolite production has not been appreciated. Therefore, the present invention provides a description of how the unique capabilities of embryogenic tissue cultures of Taxus may be used to produce taxol and related taxanes.

The present invention is based on the observation that in vitro cultured primary explants obtained from plants of the genus Taxus, produce and secrete compounds which inhibit somatic embryogenesis. Based on this observation, the present invention provides methods of inducing somatic embryogenesis from cultures and primary explants of Taxus. Specifically, embryogenic tissue can be obtained from explants of the genus Taxus by first culturing a Taxus explant in a culture media and, second, successively transferring the explant to fresh media during culture to obtain early stage somatic embryos.

The present invention further provides methods of clonally propagating plants from the genus Taxus. Specifically, plants of the genus Taxus can be clonally propagated by (1) culturing a Taxus explant in a culture media, (2) successively transferring the explant to fresh media during culture to obtain embryogenic tissue, and (3) transferring embryogenic tissue to media capable of inducing the somatic embryos contained therein into plants.

The present invention further provides methods of producing genetically altered plants of the genus Taxus. Utilizing the methods of the present invention for the induction of somatic embryogenesis, it is now possible to regenerate whole plants from a genetically altered, single Taxus cell. Plants produced in this fashion can be selected for their ability to produce elevated levels of taxol or taxane-ring containing alkaloids, or for the ability to grow under specific physiological conditions. Specifically, the present invention is related to methods of generating variant plants of Taxus which overproduce taxane-ring containing alkaloids. These variants can be selected from naturally occurring variants which appear during in vitro propagation, generated through chemical or physical mutagenesis, or obtained as a result of being transformed with an exogenously supplied DNA.

Hence, a preferred embodiment of the invention relates to a method of producing genetically altered plants of the genus Taxus comprising the steps of: culturing explants from the genus Taxus in a culture media under conditions which produce somatic embryos; introducing DNA into said embryos to produce genetically altered embryos; and regenerating plants from said altered embryos.

Another preferred embodiment of the invention relates to a method of producing genetically altered plants of the genus Taxus comprising the steps of: obtaining explants from the genus Taxus; introducing DNA into said explant; culturing said explant containing said DNA in a culture media under conditions which produce somatic embryos; and regenerating plants from said somatic embryos.

Moreover, an embodiment of the invention relates to genetically altered PNEs. Utilizing the methods of the present invention for the induction of somatic embryogenesis and production of PNEs, it is now possible to induce development of genetically altered somatic embryos to genetically altered PNE tissue. Hence, the invention relates to generating variant PNEs which produce increased amounts of various compounds. These variant PNEs can be selected from naturally occurring variants which appear during in vitro propagation, generated through physical or chemical mutagenesis, or obtained as the result of being transformed with an exogenously supplied DNA. A single plant cell can be transformed with desired DNA, and the transformed cells can be induced to undergo somatic embryogenesis and precocious germination to form transgenic precocious neomorphic embryoids (tPNEs) according to the methods of the present invention.

The present invention is additionally based on the surprising observation that in vitro propagated somatic embryos of Taxus produce taxane-ring containing alkaloids. This result is surprising because taxol has not been reported to occur in embryos. Moreover, it would not have been expected that a secondary metabolite such as taxane-ring containing alkaloids could have been produced in somatic embryos, since such embryos are believed to lack the requisite biochemical machinery for producing such secondary metabolites.

Moreover, the present invention relates to making variant PNEs of Taxus which overproduce taxane-ring containing alkaloids.

Taxol and related taxanes are diterpenes, that is, they are members of a class of molecules (terpenes) containing a twenty carbon ($C_{20}$) framework. The carbon framework is biosynthetically assembled by the sequential condensation of isopentyl phosphate (IPP)- monomeric isoprene ($C_5$) units. Thus, diterpenes like taxol contain four isoprene units. The enzymes that are responsible for the sequential condensation of isoprene into first geranyl pyrophosphate (GPP; $C_{10}$), followed by farnesyl pyrophosphate (FPP; $C_{15}$) and finally, geranylgeranyl pyrophosphate (GGPP; $C_{20}$) are compartmentalized. The enzymes that elaborate these $C_{10-20}$ frameworks into mono-, sesqui-, and diterpenes may or may not be compartmentalized in organelles.

In conifers, the enzymes responsible for producing GPP, FPP, and GGPP are found only in mature plastids, either chloroplasts or leucoplasts (Bernard-Dagen, C. (1987), "Biosynthesis of lower terpenes. Genetic and physiological controls in woody plants". In *Genetic Manipulation of Woody Plants*, Hanover and Keathley, eds., Plenum Press, pp. 329–351). Chloroplasts are known primarily for their function in photosynthesis, but leucoplasts are less familiar. As their name suggests, leucoplasts are colorless plastids and represent a transitory type between the immature plastids (proplastids) found in actively growing regions of the plant (e.g., shoot tip or cambium) and mature, specialized plastids such as chloroplasts, amyloplasts (starch containing), and chromoplasts (pigment containing). Tissues that lack these mature plastids are thought to be incapable of synthesizing all classes of terpenes.

Some consequences of the localization of terpene biosynthesis to only those tissues with mature plastids are known from experience. For example, deciduous trees are often defoliated by pests such as the gypsy moth. However, this cannot be said of conifers (evergreens). That is because monoterpenes, synthesized and stored in chloroplast-containing conifer foliage, are extremely bitter as well as toxic to most insects. Rather, most insect pests of conifer have names such as the Nantucket Tip Moth, or the Larch Sawfly. These pests are able to digest conifers by restricting their attack to tissue that does not contain terpenes such as apical meristems (tip moth) or cambial meristems (sawfly). Not surprisingly, the lack of terpenes in these tissues is corroborated by microscopic examination that reveals that they contain only undeveloped proplastids.

As gourmet cooks can attest, pine nuts make a pleasing addition to sauces in many delicately flavored dishes, such as fish. Pine nuts are pine seeds in which the seed coat has been removed, leaving behind the endosperm and embryo. If pine nuts contained terpenes, like the virtually inedible orange peel, they could not be used to accent such mild flavored dishes such as fish.

Conifer embryos have been shown to contain only embryo-specific plastids (Wann et al., "Norway Spruce as a model system for embryogenesis in conifers," in *Proceedings-TAPPI Research and Development Conference* Raleigh, N.C. (1986), pp. 131–13) which others have termed proplastids (Tautorus et al., *Can. J. Bot.* 69:1873–1899 (1991)), that are very similar to the immature, undeveloped proplastids found in the meristems of conifers. The observation that conifer embryos and embryogenic conifer tissue lack mature plastids argues strongly for the lack of terpenes in embryogenic conifer tissues. The lack of mature plastids means that any IPP produced (which is formed in the cytosol) cannot undergo the chain elongation reactions necessary for terpene production as the organelles in which the reactions occur are absent. Indeed, all evidence in the literature, known to the Applicant, teaches that embryos or embryogenic tissue would be the last place to look for all classes of terpenes including diterpenes like taxol. In contrast, callus tissue contains mature plastids and, therefore, it was expected that these cells would produce taxol. However, totally unexpectedly, it was found that embryogenic tissue produces taxol.

Utilizing in vitro cultures of embryogenic tissue, it is now possible to produce large amounts of taxane-ring containing alkaloids. Embryogenic tissue offers the advantages of the rapid growth rate associated with callus cultures for the production of large quantities of tissue, while at the same time affords the proliferation of structures (somatic embryos) that sequester taxanes. Taxane-ring containing alkaloid compounds from somatic embryo cultures of Taxus can be obtained by first culturing explants from the genus Tayus in a culture media under conditions which produce somatic embryos, or somatic seedlings and second, isolating the taxane-ring containing alkaloid compounds from the somatic embryos or the culture media.

More specifically, using the PNEs of the present invention, production of taxanes can be significantly increased over that produced in somatic embryos. To obtain increased production of taxanes, Taxus somatic embryos are stimulated in vitro to develop and mature into PNEs which have some of the characteristics of seedlings. The Taxus PNEs of the present invention produce significantly increased amounts of taxanes as compared to those produced in embryogenic tissue.

BRIEF DESCRIPTION OF THE FIGURES

FIG. 3 shows a summary of induction of somatic embryogenesis from a number of varieties of Taxus.

DETAILED DESCRIPTION OF THE INVENTION

Figure 1:
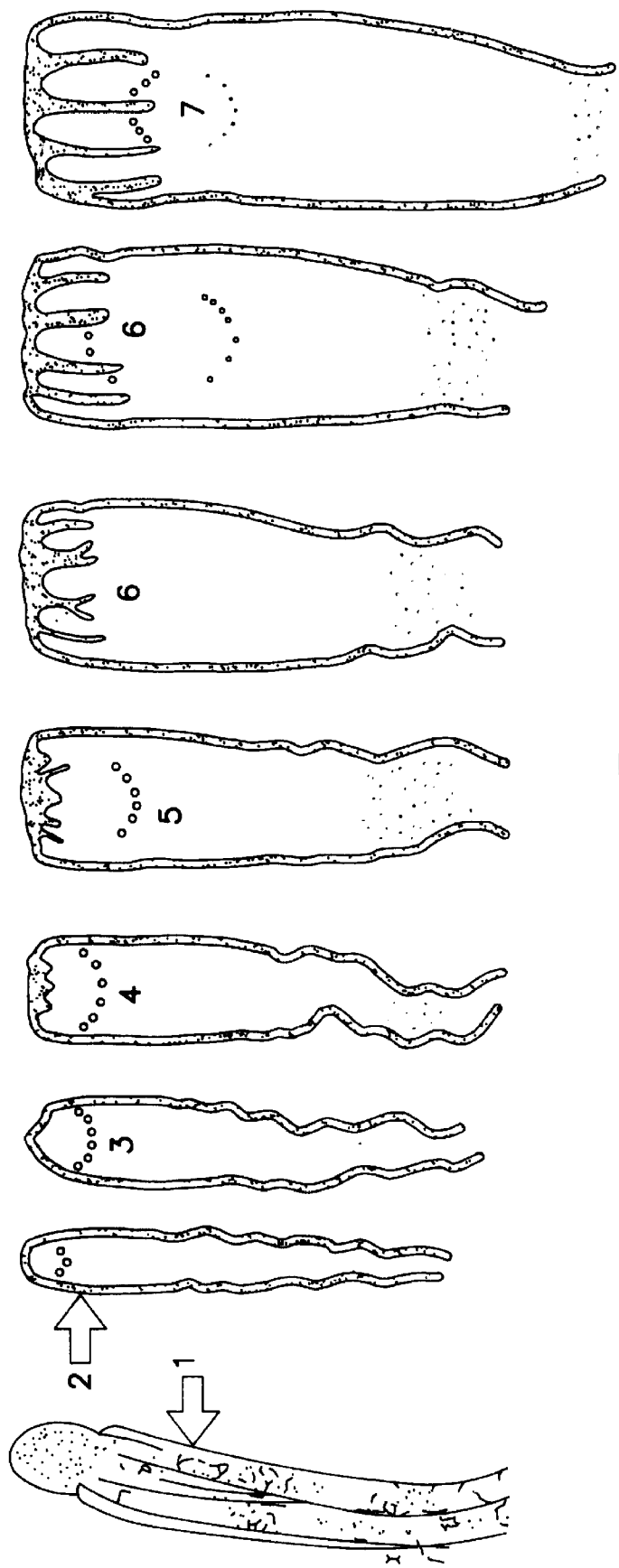
FIG. 1 shows the typical stages of development of embryos in the Coniferales.

I. Induction of Development and Maturation of Somatic Embryos into Precocious Neomorphic Embryoids Somatic embryo development can be triggered by removing or lowering the concentration of growth regulator(s) (typically auxins and/or cytokinins) used to perpetuate the embryogenic condition. Removal or dilution of growth regulators stimulate the somatic embryos to develop in a manner similar to zygotic embryos in developing seed. However, by appropriate adjustment of the culture media, somatic embryos can be stimulated to form a tissue, called herein precocious neomorphic embryoids (PNE), instead of a normal seedling. Examples of appropriate adjustment of the culture media for making PNEs instead of seedlings include maintaining or increasing the level of an organic form of reduced nitrogen like glutamine or casein hydrolysate so that the medium contains a high amount of reduced organic nitrogen. In addition, excluding plant growth regulators (PGRs) such as abscisic acid (ABA) is also an important way to encourage PNE formation. This process, as described above, is known as "precocious germination". In this process, embryos are induced to skip or truncate the late stages of embryo development (a.k.a. "ripening") and attempt germination. In so doing, the later stages of embryo development are not reached, hence, germination is incomplete, and a seedling is not produced. Instead, a PNE is produced which produces high levels of taxane commensurate with that produced in seedling tissue.

The conditions that lead to PNE formation have not been well described per se. Rather, they are elucidated indirectly, as taught herein. Nor have the formation and physiological properties of PNEs been directly investigated. As described in the present specification, investigation of the conditions that will support embryo maturation and normal germination simultaneously and conversely outline the conditions for PNE formation. PNEs, which were previously regarded as impediments to normal embryo development, have been shown in the present invention to provide a new source for controlled production of secondary metabolites and other biological products.

The principle use of somatic embryogenesis has been plant propagation, and formulating the conditions that will support high frequency embryo maturation, and germination has been the center of attention. A barrier to plant propagation via somatic embryogenesis has been precocious germination of embryos as described above. Due to the problem of precocious germination, attempts to minimize or avoid it have been made so that normal embryo development can be completed. Investigating the conditions that will support normal embryo maturation has conversely and simultaneously outlined in an indirect way, details of the conditions that will support the formation of PNEs.

The process of producing somatic embryos in hundreds of plant species, both gymnosperms and angiosperms, is known to the extent that a generalized protocol for the process can be described. As noted above, the conditions that will encourage precocious germination and the production of PNEs can also be stated with enough precision such that those skilled in the art could produce without undue experimentation PNEs of any species in which somatic embryogenesis has been reported. In those plants in which biologicals accumulate in non-seed tissue, the following description will, without undue experimentation, describe a system for the production of any natural product using PNEs.

Methods

Somatic embryogenesis in tissue culture, first confirmed in 1958 for carrot has been reported in 132 species of angiosperms (Tisserat et al., *Hort. Rev.* 1:1–78 (1979)) and 21 species of gymnosperms (Tautorus et al., *Can. J. Bot.* 69:1873–1899 (1991)) notably the conifers and cycads. The procedure for the initiation of somatic embryogenesis in all these species are very similar. Hence, the following is a general protocol which can be universally applied to these plants without undue experimentation.

Somatic embryos are produced by cultures of immature embryo explants on any one of dozens of typical plant tissue culture media that feature macro and microelements, myo-inositol, and a carbon source such as sucrose with a total osmotic potential on the order of 100–400 mmol/kg. These media are supplemented either alone or in combination with an auxin and a cytokinin (PGRs). A principle auxin used is 2,4-dichlorphenoxyacetic acid (2,4-D) and a principle cytokinin is benzyladenine. The concentrations of these plant growth regulator compounds are usually from 0.01–100 mg/L and are usually arrived at empirically without undue experimentation. Successful initiation of somatic embryos is usually observed over a considerable range of PGR concentrations. A starting PGR concentration of 1–5 mg/L is typically chosen. Once somatic embryogenesis has been initiated, it can be perpetuated on the same medium, occasionally under reduced concentrations of auxin and cytokinin. In some cases, cytokinin alone will support the continued proliferation of somatic embryos. In others, no growth regulators are necessary after initiation. The cultures are usually initiated in the dark, but in many species initiation will proceed in the light as well.

The classical "trigger" for switching from somatic embryo proliferation to embryo maturation is the removal or dilution of the PGRs. In many species this action alone will be sufficient to stimulate normal development of a certain proportion of the somatic embryos into plants. Early in the history of somatic embryogenesis, low conversion efficiencies (defined as the percentage of the total somatic embryos that develop into plants) for somatic embryos were ignored. However, as many tried to make somatic embryogenesis a plant propagation process, it became imperative that conversion efficiency be increased. Thus an understanding of the factors that reduce conversion efficiency became an active area of research. It was against this background that precocious germination was soon identified as significant impediment to successful conversion of somatic embryos into plants.

Investigation into embryo maturation in plants led to an understanding that both moisture stress and the naturally occurring growth regulator, abscisic acid (ABA) play an important role in the process. At the very earliest stages of embryo maturation, elevated levels of osmotic pressure in the milieu surrounding the embryo were found to be important to attain mid-stage maturity. Once mid-stage embryo maturity was achieved, ABA was found to be important for further maturation. ABA triggers the accumulation of storage products in the embryo as well as the ability to tolerate desiccation—factors critical to successful embryo germination and concomitant plant formation.

In somatic embryogenesis, supplementing tissue culture media with ABA was key to inhibiting precocious germination and allowing maturation of somatic embryos in vitro. In turn, improved maturation translated into higher conversion efficiencies. Increasing the osmotic pressure in the early stages of development was not always necessary, as tissue culture media is often sufficiently high enough in osmotic pressure (about 150 mmol/kg) to support embryo development in the early stages. Reducing the level of reduced organic nitrogen (e.g., glutamine or casein hydrolysate) present in the media also promoted normal maturation, as this action was thought to encourage the accumulation of storage proteins, some of which were required for desiccation tolerance in the late stages of embryo development.

Therefore, the conditions for somatic embryo maturation can be readily described, as set forth below, for species in which somatic embryogenesis has been reported.

Embryogenic tissue or somatic embryos are transferred from tissue culture medium containing growth regulators to one devoid of growth regulators or with levels reduced from the maintenance medium by about a factor of ten. For embryogenic cultures with a high moisture content, an intermediate transfer to medium containing an adsorbent material such as activated charcoal (0.1–1%) can help to absorb excess PGRs dissolved in the cultures. This medium may or may not be adjusted to an osmotic pressure of about 150–400 mmol/kg. When embryos have developed to the precotyledonary stage (a stage easily identified visually as the point just before the seed leaves are formed), that levels transferred to a medium containing ABA at levels from about 0.1–50 mg/L to complete development. Again, the osmotic pressure may or may not be increased to the range described above.

The procedure described above, has basically been formulated to initiate somatic embryogenesis and subsequently induce somatic embryos to mature in a process analogous to that found in seed. Mimicking the maturation process found in seed produces well-formed embryos that have a capacity for normal germination and plant formation. Since the precocious germination was a principle barrier to normal maturation and development, the conditions described above conversely outline the condition for the production of PNEs.

For making PNEs, the procedure for the initiation of somatic embryogenesis is the same as above. However, for embryo maturation, the following changes are required so that instead of mature embryos, PNEs are produced.

Induction of embryo maturation from the proembryo to the early-stage is by removal or dilution of PGRs and increasing osmotic pressure if necessary. Once mid-stage development has been achieved, the embryos are transferred to the same or similar medium lacking ABA but containing high levels (i.e., 50–5,000 mg/L, preferably 2,500 mg/L; or as percentages, up to 0.45%, preferably up to 0.2%) of reduced organic nitrogen source, like glutamine or casein hydrolysate.

In precocious germination, it is primarily the late stages of embryo development that are skipped, so it is important that the morphogenetic program for embryo maturation is initiated to ensure tissue determination for embryo maturation and not dedifferentiation or other unorganized and ultimately unproductive growth. The level of embryo development required before somatic embryos will be "locked" into a maturational program can easily and rapidly be empirically determined by observing the opacity of the maturing embryos. Soon after the earliest or proembryo stage, embryos turn from translucent to opaque in appearance as the accumulation of storage products begins. For good PNE formation, just before this point has been reached, the mid-stage embryos are transferred to medium lacking ABA and containing elevated levels of reduced organic nitrogen.

Applications

Figure 9A:
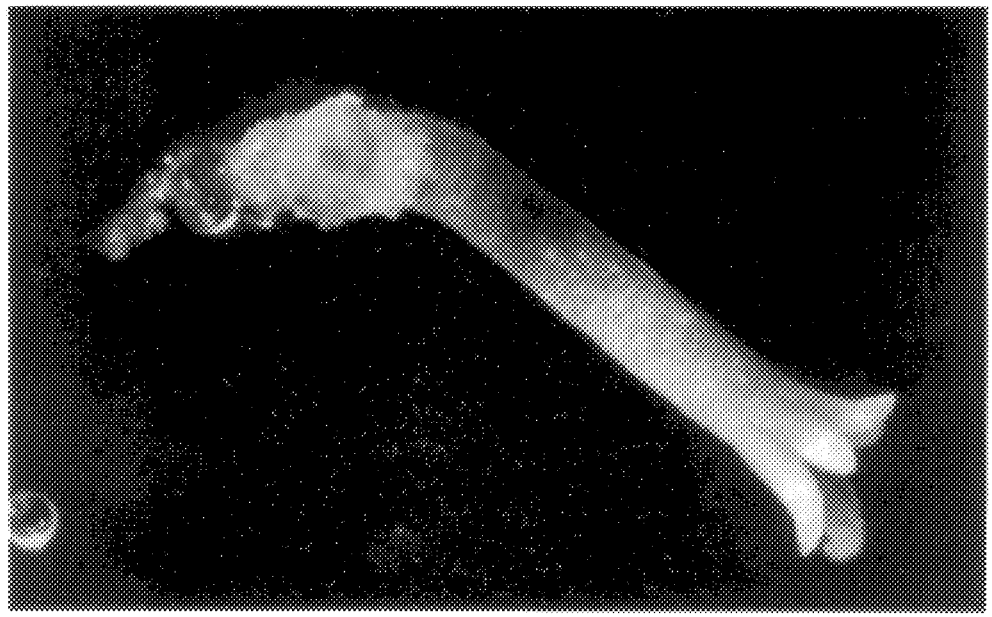
FIG. 9 shows a photograph of Taxus precocious neomorphic embryoids (PNEs) (see Panels C and D) and coniferous (i.e., Picea) germinating somatic embryo seedlings (see Panels A and B). The striking differences and similarities between PNEs and seedlings are readily apparent.
Figure 9B:
Figure 9C:
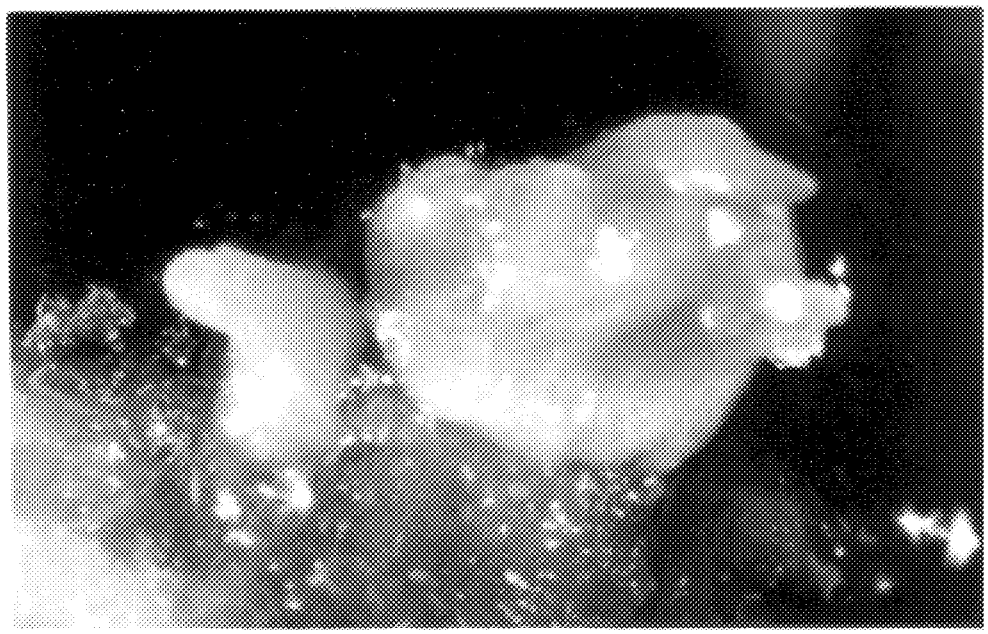
Figure 9D:
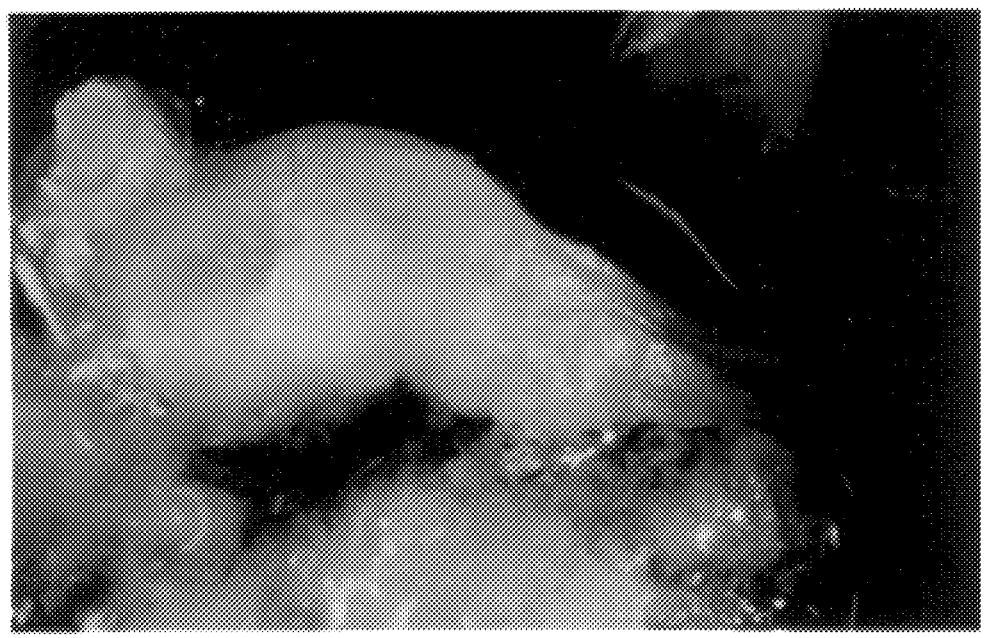
Figure 10:
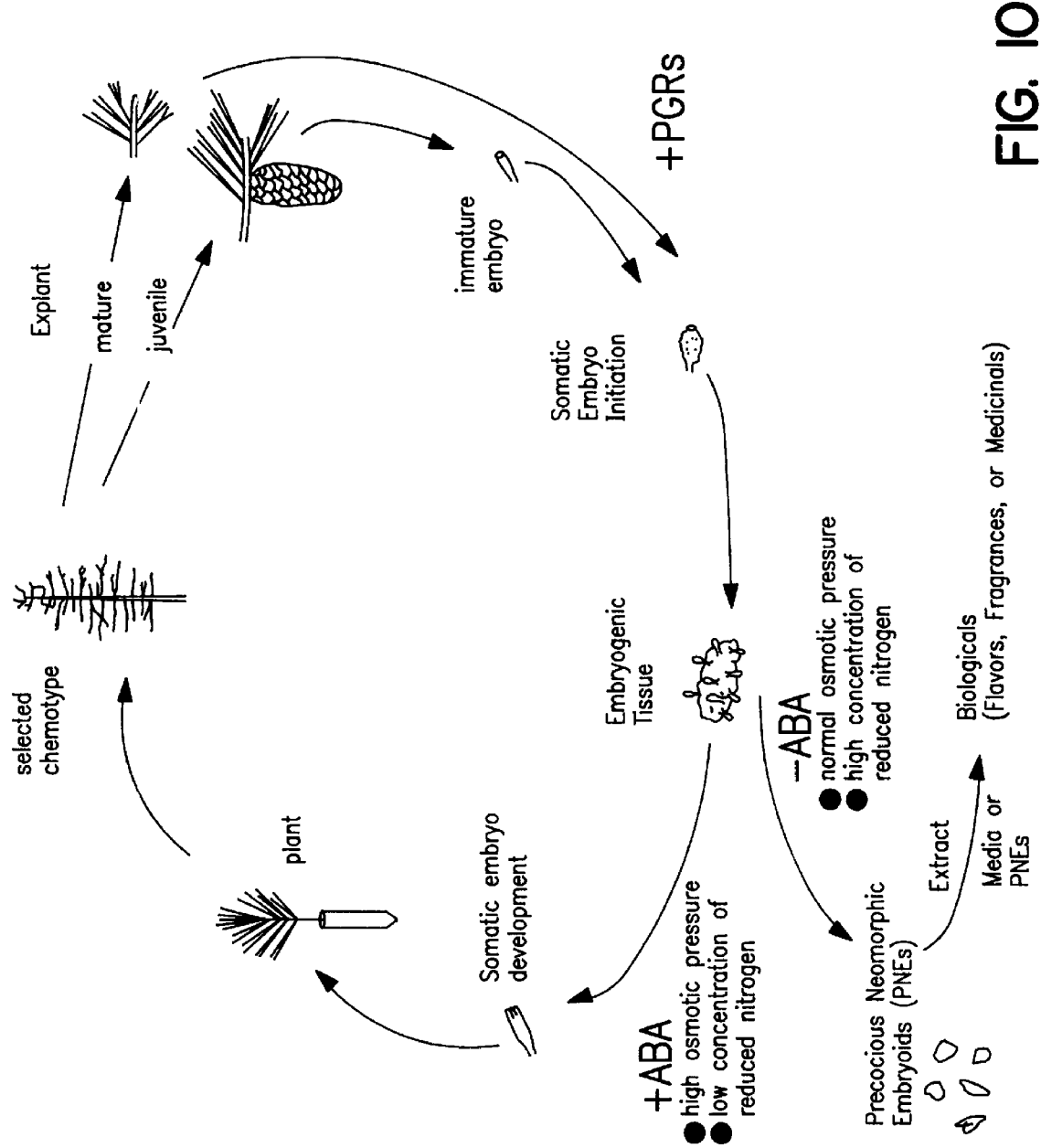
FIG. 10 shows the use of somatic embryogenesis for plant formation or for the production of biologicals through PNEs. "PRGs" stands for plant growth regulators and "ABA" stands for abscisic acid.

As precocious germination proceeds, PNEs assume features similar to mature embryos and later, seedlings. However, it is soon visibly apparent that something has gone awry in the embryo maturation. Often, PNEs will have fused cotyledons, or cotyledons in place of a shoot apex, or only half of the embryo axis is formed (i.e., either the shoot or the root). Some of the more common PNE types are shown for Taxus in FIGS. 9C and 9D. It is readily apparent from these photographs that PNEs depart from the normal embryo development program typified by another conifer, Picea, in FIG. 9, Panels A and B. Even though PNEs do not give rise to plants, they produce seedling tissue, as indicated by the green color characteristic of chlorophyll found in seedling or stem tissue. It is this tissue that can produce biologicals which are characteristic of the intact plant, and not the embryo.

Table 1 shows a list of species of flavor, fragrances, medicinal and alkaloid-producing plants in which somatic embryogenesis has been reported. These plants are suitable candidates for PNE based production systems described above.

TABLE 1

Species or Flavor, Fragrance, Medicinal and Alkaloid-producing Plants in Which Somatic Embryogenesis have been Reported[1]

| | |
|---|---|
| *Aconitum Noveboracense* | *Dioscorea* spp. (sapogenin) |
| *Allium sativum* (onion flavor) | *Fagopyrum esculentum* |
| *Amni majus* | *Foeniculum vulgare* (fennel oil) |
| *Angelica* spp. (angelica oil) | *Hyoscamus niger* (scopolamine) |
| *Apum graveolens (celery oil)* | *Lavandula* spp. |
| *Atropa belladonna* (atropine) | *Panax ginseng* (ginesenosides) |
| *Bupleurum falcata* | *Paparver* spp. (morphine) |
| *Carum carvi* (caraway oil) | *Petroselinum crispum* |
| *Cassia fistula* | *Pimpinella anisum* (anise) |
| *Coffea arabica* (caffiene) | *Punica granatum* |
| *Coptis japonica* | *Quercus* spp.[2] (quercitin) |
| *Coriandrum sativa* (coriander) | *Tylophora indica* |

TABLE 1-continued

Species or Flavor, Fragrance, Medicinal and Alkaloid-
producing Plants in Which Somatic Embryogenesis have
been Reported[1]

| | |
|---|---|
| Datura innoxia (tropane alkaloids) | Urginea indica |
| Digitalis spp. (cardiac glycosides) | Taxus spp.[3] (taxol) |
| | Zingiber officinale (ginger oil) |

[1]Adapted from Y. P. Bajaj et al, Biotechnology in Agriculture and Forestry Vol. 4, Medicinal and Aromatic Plants (1988), pp. 63–70; except as noted.
[2]Gingas & Lineberger, Plant, Cell, Tissue and Organ Cult. 17:191–203 (1989).
[3]This work.

Table 2 provides a list of species which are (1) still cultivated to produce economically important biologicals or are slow growing and/or produce biologicals in such low quantity that an alternative to plant cultivation would be highly desirable, or (2) produce biologicals that are difficult to produce by chemical synthesis. The biologicals in Table 2 would be good candidates for the large scale cultivation and extraction of PNEs, even though somatic embryogenesis has not been reported in this species. However, lack of such reports does not indicate that they cannot be induced to undergo embryogenesis by the well-known methods available in the are. By following the procedure outlines for the induction of somatic embryogenesis and the formation of PNEs, production of the active principles in each of these species is now possible.

TABLE 2

Candidate Plant Species for PNE Production Based on
Supply or Difficulty in Synthesis

| | |
|---|---|
| Ancistrocladus spp. | Iris spp. (irones) |
| Baccharis megapotamica (baccharin) | Ochrosia moorei (ellipticine) |
| Brucea antidysenterica (bruceautin) | Pancratium littorale |
| Calophyllwu lanigerum | Physostigma veneosum (physostigmine) |
| Camptotheca accuminata (camptothecin) | Pelagonium spp. (geranium oil) |
| Catharanthus roseus (vincristine) | Pilocarpus spp. (cholinergics) |
| Cephalotaxus harringtonia (harringtonine) | Pogostemon cablin (patchouli) |
| Chondodendron tomentosum | Putterlickia verucosa (maytansine) |
| Cinchona spp. (quinine) | Roscmarinus officinalis (rosemary) |
| Cinnamomum Cassia (cassia) | Strychnos spp. (curare) |
| Cinnamomum camphora (linalool) | Tripterygium wilfordii (triptolide) |
| Cymbopogon spp. (lemongrass) | Valariana officinalis (valerian oil) |
| Erythroxyion coca (cocaine) | Vetiveria zizanoides (vetiver oil) |
| Heliotropium indicium (indicin-N-oxide) | |

II. Induction of Somatic Embryogenesis in Explants From Varieties of Taxus

The present invention is based on the observation that primary explants and in vitro cell cultures derived from plants of the genus Taxus, especially *T. brevifolia*, produce compounds which inhibit somatic embryogenesis. Based on this observation, it can be inferred that taxane-ring containing alkaloids are being produced. Thus, the present invention provides methods of inducing somatic embryogenesis from primary explants of varieties of Taxus, especially *T. brevifolia* (FIG. 3).

Specifically, the method comprises the steps of: culturing an explant from a plant of the genus Taxus in a media capable of promoting the induction of somatic embryogenesis, transferring the explants to fresh media during culturing to remove the cultured cells from the inhibitors which are produced, and isolating the somatic embryos produced in the culture.

As used herein, a "somatic embryo" consists of a cell or group of cells having the potential to become a plant by developing along a route that mimics the course of development a zygotic embryo undergoes, within a seed. In conifers, as in most plants, somatic embryogenic cells can be classified into two stages (FIG. 1). The first stage consists of proembryogenic masses and early-formed somatic embryos (see stage 1 in FIG. 1), and the second stage consist of further differentiation and development of the early-formed embryos to embryos (stages 3–6). The proembryogenic mass is a group of cells having the potential to become an embryo but lacking defined meristematic organ primordia. It is these rudimentary stages of embryo development that proliferate as long as the cultures are maintained on media with 2,4-D and BA.

Upon transfer of embryogenic tissue cultures to a medium that supports embryo maturation, embryo development proceeds along a pathway analogous to that found in seeds. The stages in this pathway are illustrated in FIG. 1.

By the final stage of embryogenesis (Stage 7), ripe, cotyledonary embryos are produced which possess a well defined elongated bipolar structure containing an apical meristem and cotyledon primordial at one end and a radical meristem at the opposite end. Cells within these embryos are typically characterized as containing seed storage proteins, lipids, and are cytoplasmically dense.

Embryogenic conifer tissue differs significantly from callus cell cultures and it may be argued that they cannot be called callus cultures. Callus cultures are considered to be an unorganized growth of undifferentiated cells that are either unconnected or loosely connected and can be generally produced by culturing a variety of explants. Unlike cells found in embryogenic cultures, callus cells tend to be spherical, isodiametric, highly vacuolated with non-dense cytoplasms. Callus cells are considered to be dedifferentiated or undifferentiated plant cells since they are derived from the rapid cell division of differentiated plant explants.

Embryogenic tissue, on the other hand, is comprised of masses of (1) very early stage embryos, (2) cells in the process of producing early stage embryos (i.e. proembryogenic masses) or (3) suspensor-type cells that have been sloughed off by the early-stage embryos. Therefore, the cultures have an aspect of organization to them, as well as consisting of cell and tissue types, that are strikingly dissimilar by inspection under a low power microscope.

In addition to physical appearance, callus cells and embryogenic cells are different at the biochemical and histological level as indicated by differences in a number of biochemical markers such as ethylene evolution rate, concentrations of glutathione, the ability to reduce ferric ion, protein synthesis rates, and plastid structure. (Wann et al., *Plant Cell Reports* 6:39–42(1987); Wann et al., *Trees* 3:173–178 (1989)).

As used herein, a "primary explant" is any tissue or cells obtained from a plant. This includes, but is not limited to, zygotic embryo tissue, root or shoot meristematic tissue, and cambium tissue. The most preferred tissue is obtained from immature arils and consists of zygotic embryos, as well as cotyledonous, and hypocotyledonous cells.

Any Taxus variety can be used as a source of the explant. This includes, but is not limited to, *T. brevifolia, T. baccata, T. x media*, and *T. cuspidata*.

Prior to culturing, the explant is surface sterilized to kill potential contaminants such as bacteria or fungus which may be present on the explant surface. The most commonly employed method involves immersion of the explant in a solution of bleach and a wetting agent such as Tween-20™.

Such an immersion sterilizes the surface of the explant while not effecting the underlying cells. A vacuum can be employed during immersion in order to aid the sterilant in surface penetration. Once the explant has been obtained and treated, it is placed in a liquid or on solid culture media.

In general, most plant growth media which have been shown to be effective in inducing somatic embryogenesis in other conifers can be utilized in generating somatic embryos from varieties of Taxus. These include, but are not limited to BLG (Wann et al., *Trees* 3:173–178 (1989) herein incorporated by reference), MS (Gupta et al., *Bio/Technology* 5:141 (1987) herein incorporated by reference), BMI (Krogstrup, *Can. J. For. Res.* 16:664–668 (1986), herein incorporated by reference), and DCR (Gupta et al., *Plant Cell. Rep.* 4:177 (1985), herein incorporated by reference). Most preferred are medias which contain the plant hormones 2,4-dichlorophenoxyacetic acid (2,4-D) and benzyl adenine (BA) as well as casein hydrolysate. One skilled in the art can readily adapt such medias for use in the present invention without undue experimentation. In the example provided below, BLG media is employed.

Various conditions may be employed in the culturing of the primary explants. Conditions such as temperature and lighting will vary slightly from plant variety to plant variety as well as tissue source. For *T. brevifolia*, culturing is most preferably performed in the dark and from about 20°–25° C. One skilled in the art will readily vary culture conditions to optimize both cell proliferation and embryo production.

The length of time an explant needs to be cultured before somatic embryogenesis is induced will vary depending on the source of the explant, culture conditions, and frequency of transfer. For immature embryo explants of *T. brevifolia*, cultured in BLG-casein media at 22° C., no light, with transfers from about every two to four weeks, embryogenic tissue will be induced in about 6 weeks.

As used herein, "transferring said explant" refers to the process of supplying fresh media to the explant. Transferring effectively removes the explant from the inhibitors of embryogenesis which are secreted by varieties of Taxus. This need for transferring in order to induce and maintain somatic embryogenesis is unique amongst conifers.

Procedures for transferring the cultured tissue will vary depending on the type of media employed. When the explant is maintained on solid media, transferring entails the removal of the explant from the old media to a new media. The inhibitors of embryogenesis produced by growing cultures of Taxus do not rapidly diffuse through solid media. Therefore, the explant may be removed from the secreted inhibitors by simply placing the cultured explant on a fresh surface of the culture plate.

Figure 2A:
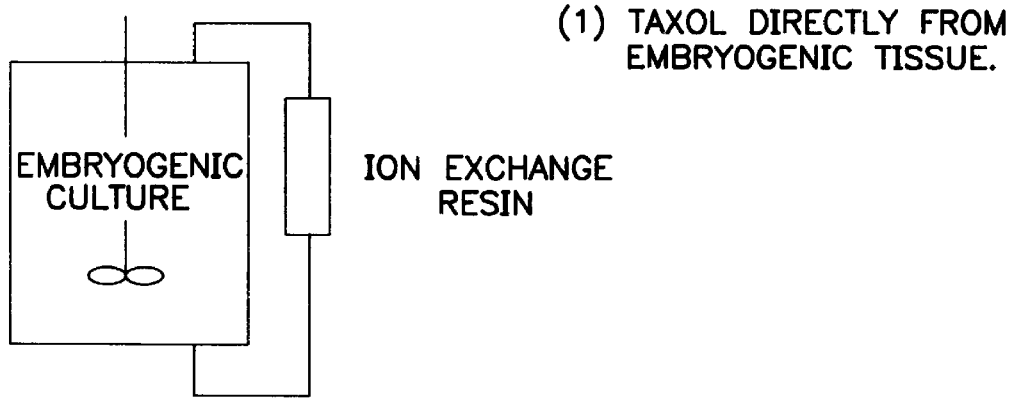
FIG. 2A and 2B show a continuous flow liquid culture system for the production of somatic embryo (a) and taxane-ring containing alkaloids (b).

Somatic embryogenesis may also be induced in liquid cultures of Taxus. Embryogenic tissue can be removed from the liquid media via filtration or sedimentation to allow fresh media to be supplied. Alternatively, a continuous flow system can be employed to supply the cultured tissue with fresh media. In such a system, the tissue is maintained in an environment that allows media to flow through the environment while restricting the flow of the cultured cells (See FIG. 2A).

The length of time between transfers will vary depending on the source of the explant, culture conditions, media, as well as the cell density in the culture. In general, when solid media is employed, such transfer will be performed about every 2–3 weeks. One skilled in the art will be readily able to determine the time between transfer by visually observing the rate of production of somatic embryos.

Once a culture producing somatic embryos is obtained, the embryos can be matured, isolated and germinated to form seedlings. Any procedure known in the art for embryo maturation can be employed. These typically involve a transfer of embryogenic tissue to a medium with increased osmolarity and containing abscisic acid (ABA). (See Becwar et al., *Tappi Journal* 70 (4):155–160 (1987).)

The present invention further provides cultured Taxus embryogenic tissue. Such tissue is obtained using the methods described above. Any Taxus variety can be utilized. This includes, but is not limited to *T. brevifolia, T. baccata, T. x media,* and *T. cuspidata.*

Utilizing the techniques described above, plants from the genus Taxus can now be clonally propagated from somatic embryos.

A plant from which clonal offspring is desired, may be used as a source of the primary explant. Through successive culture transfers, somatic embryogenesis of the primary explant can be induced as described above. The embryos thus produced can be readily regenerated into whole plants and thus generate plants which are clonally derived from the explant. (See Beewar et al., *Tappi Journal* 70 (4):155–160 (1987); Durzan et al., *Plant Science* 52:229–235 (1987); Krogstrup et al., *Plant Cell Reports* 7:594–597 (1988), herein incorporated by reference).

Additionally, the above described methods can be used to propagate plants which are variants of the explant source.

As used herein, a "variant" is defined as any plant or tissue which contains a genetic alteration not present in the plant from which the explant is derived from. This may include a change in ploidy level, a change in the sequence of a particular segment of DNA, or the introduction of an exogenously supplied DNA sequence. The variant may be generated naturally during the process of tissue culturing, or can be generated through biochemical, physical, or molecular techniques.

Since plant cultures tend to be genetically unstable, naturally occurring variants may be produced during prolonged culture. Such variants can be assayed for a change in a physiological characteristic, such as accelerated growth, the level of production of a plant metabolite or alkaloid, or a change in ploidy level. Preferably, such variants will exhibit increased production of taxol or a taxol precursor. Once identified, the variant cell or cells can be isolated and used to produce clonally propagated plants with increased taxol or taxol precursor content as described above.

In addition to naturally occurring variants, variants may be generated through a variety of methods known in the art. These include, but are not limited to, physical or chemical mutagenesis, protoplast fusion, or direct transfer of exogenous DNA. Such methods can be used to induce variants in the primary explant prior to the initiation of somatic embryogenesis, or to the somatic embryos which have been generated using the methods described herein.

Physical or chemical mutagenesis entails exposing the cultured cells or primary explant to an agent which is capable of inducing DNA damage or inhibiting chromosome segregation during meiosis and mitosis. Such agents include UV light, ethylinethylsulfonate, nitrous oxide, acridine orange, colchicine, and nitrosoguanidine. Agents such as these have been employed in a variety of systems to introduce random changes in the DNA of the organism in order to generate variants. (Chaleff, R. S., *Science* 219:676–682 (1983).)

Hence, a preferred embodiment of the present invention relates to a method of producing variants of plants from the genus Taxus which produce elevated levels of taxane-ring containing alkaloids comprising the steps of: culturing explants from the genus Taxus in a culture media under conditions which produce somatic embryos; inducing mutagenesis in said explants with a capable agent; selecting embryos which produces said elevated level of taxane-ring containing alkaloid; and regenerating plants from said selected embryos.

While the site of mutagenesis and the resulting variant produced is not predetermined, one skilled in the art can readily adapt known mutagenesis and selection procedures to the explants and embryogenic culture of the present invention.

The mutagenized cells may be screened for an alteration in the production of a secondary metabolite such as the taxane-ring containing alkaloids of the present invention. Preferably, such mutants will over produce the taxane-ring containing alkaloids. Methods for detecting the level of taxane-ring containing compounds include HPLC (See Examples) and by immunologically reacting a sample of the culture media with an antibody specific for such taxane-ring containing alkaloids. (See Stephen M. Edington, Bio/Technology 9:933–938 (1991).)

Protoplast fusion can be utilized to generate variants with increased ploidy levels as well as to produce plants containing chromosomes from other varieties. For example, by fusing a taxol or taxol-precursor producing variety of Taxus with a non-producing variety, a variant may be generated which processes the characteristics of both varieties.

Variants can also be produced through the introduction of exogenously supplied DNA. (Ellis et al., *International Society of Plant Molecular Biology*, meeting of Oct. 6–11, 1991, Tucson, Ariz.). As described earlier, numerous techniques have been developed to introduce DNA into a plant cell. These include, but are not limited to, engineered Ti plasmids from the soil bacterium *A. tumefaciens* (Czako, M. et al., *Plant Mol. Biol.* 6:101–109 (1986); Jones, J. D. G. et al., *EMBO J.* 4:2411–2418 (1985); Feirer et al., *Proceedings 20th Southern Forest Tree Improvement Conference*, Jun. 26–30, 1989, Charleston, S.C., page 381), engineered plant viruses such as the cauliflower mosaic virus (Shah, D. M. et al., *Science* 233:478–481(1986)); Shewmaker, C. K. et al., *Virol.* 140:281–288 (1985)), microinjection of gene sequences into a plant cell (Crossway, A. et al., *Molec. Gen. Genet.* 202:179–185 (1986); Potrykus, I. et al., *Molec. Gen. Genet.* 199:169–177(1985)), electroporation (Fromm, M. E. et al., *Nature* 319:791–793 (1986); Tautorus, T. E. et al., *Theor. Appl. Genet.* 78:531–536 (1989), Tautorus et al., *Theor Appl. Genet.* 78:531–536 (1989), and DNA coated particle acceleration (Bolik, M. et al. *Protoplasma* 162:61–68 (1991)).

Utilizing one of these procedures, one skilled in the art can readily generate a variant which contains an exogenously supplied gene construct. In such a fashion, a variant can be produced which contains a predetermined characteristic, such as resistance to an antibiotic. Screening for such a characteristic may be done routinely by those of ordinary skill in the art and without undue experimentation.

III. Taxane-Ring Containing Alkaloid Production in Embryonic Tissues

A further embodiment of the present invention is based on the observation that in vitro propagated somatic embryos of Taxus produces taxane-ring containing alkaloids. This is a surprising observation since taxol is normally sequestered in vacuoles and somatic embryos are not highly vacuolated. Moreover, it would not have been expected that a secondary metabolite such a taxane-ring containing alkaloid could be obtained from such biochemically immature cells. Utilizing such in vitro cultures, it is now possible to produce large amounts of taxane-ring containing alkaloids. In addition, it is now possible to produce Taxus seedlings on a large scale and isolate the taxane-ring containing alkaloids therefrom. This is significant since seedlings are second only to bark as a source of taxol and its precursors. (Vidensek, N. et al., *J. Natural Prod.* 53:1609–1610 (1990).)

Specifically, taxane-ring containing alkaloids can be obtained from cultures of somatic embryos derived from explants of the genus Taxus, especially *T. brevifolia, T. baccata, T. x media,* and *T. cuspidata.*

Figure 2B:
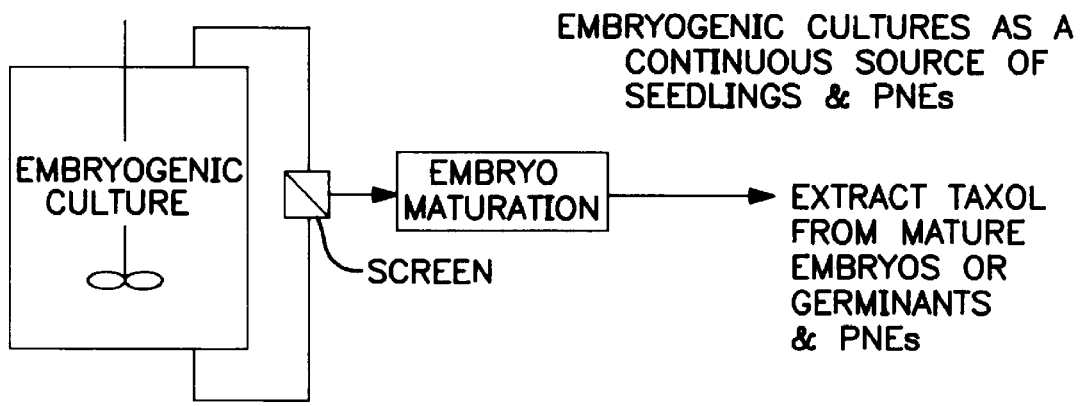

In detail, an explant is obtained from a variety of Taxus which produces the desired taxane-ring containing alkaloids. The explant is used to produce a culture which contains somatic embryos using the procedures described earlier. Taxane-ring containing alkaloids can then be isolated from either the culture media or from the tissue using techniques which are well known in the art such as column chromatography (see, Wani et al. *J. Am. Chem. Soc.* 93:2325 (1971); M. Boyd, *Personal Communication* (August 1991); (Witherup, K. M. et al., *J. Liq. Chromotgr.* 12:2117–2132 (1989)). One such system is shown in FIG. 2B.

Preferably, autoclaved fungal cells or extracts are added to the culture media to stimulate the production of taxane-ring containing alkaloids. When such fungal cell extracts are added to the media, the embryogenic tissue act to ward off the supposed infection by the production of the taxane compounds.

The most preferred embryos for isolating taxane-ring containing alkaloids are embryos from stage 7 and into germination. (See FIG. 1). Embryos from stages 1 and 2, though they may contain taxane-ring containing alkaloids, are hard to dissect and separate from non-embryogenic tissues. Embryos from stage 7 are easily separated from non-embryogenic tissues and therefore are preferred. One skilled in the art can readily adapt known procedures for isolating embryos in order to obtain any particular stage of embryo for use in the production of taxane-ring containing alkaloids.

Alternatively, fully developed seedlings produced from the embryogenic cultures, can be used as a source of the taxane-ring containing alkaloids.

The taxane-ring containing alkaloid can be isolated from media that is replaced batch-wise, or continuously. The embryogenic culture may be grown in free suspension or maybe immobilized within a carrier such as hollow fibers. Examples of such carriers are described in Durzan et al., *Plant Science* 52:229–235 (1987).

IV. Increasing Taxol Production from Somatic Embryos of Taxus

Another embodiment of the invention which relates to increasing production of taxanes in somatic embryos is based on analysis of a variety of tissue types and *Taxus brevifolia*, which indicates that seedling tissue is the second highest source of taxus. As described above, precocious neomorphic embryoids share similarities with seedlings. Therefore, it was hypothesized and successfully shown that the concentration of taxanes produced by Taxus precocious neomorphic embryoids could approach that found in seedlings. The concentration of taxanes achieved in this manner was similar to that found in callus tissue or needle tissue, which is a tissue now considered to be a "renewable" source of taxanes.

According to the method described above, embryogenic cultures, comprised of a continuously proliferating mass of somatic embryos in wide range of developmental states, *T. baccata,* cv. 'Rependens', and *T. x media,* cv. 'Hicksii', are routinely maintained and multiplied on: (1) BLCG 2/1 (see Table 3) media containing 2 mg/L 2,4- dichlorophenoxyacetic acid (2,4-D) and 1 mg/L benzyl adenine (BA) or (2) woody plant medium (WPM) (Llyod & McCown, *Int. Plant. Prop. Soc. Proc.* 30:421 (1981)) additionally containing 0.02–0.5 mg/L thidiazuron (TDZ). Both media contain casein hydrolysate at 500 mg/L and 3% sucrose.

To stimulate development of PNEs, the embryogenic cultures are transferred to media of a similar composition which lacks the growth regulators. Such media for the initial 2–4 weeks after transfer may contain activated charcoal (about 0.5%) to absorb any growth regulators carried over from the maintenance media. After several weeks, seedling-like tissue will develop as indicated by the yellow to green color that the culture takes on.

After the development of PNEs is complete, as indicated by no more greening or no further increases in size, the cultures are harvested. Taxanes can be extracted from the harvested PNE cultures by the same method used to isolate taxanes from embryogenic tissue.

Having now generally described the invention, the same will be more readily understood through reference to the following examples which are provided by way of illustration, and are not intended to be limiting of the present invention, unless specified.

EXAMPLES

Example 1

Procedure for the Initiation and Maintenance of Embryogenic Tissue in Taxus and its Subsequent Analysis for Taxol Initiation and Maintenance of Embryogenic Taxus Tissue Immature arils of Taxus species were collected throughout the summer (the best time is July) and were sterilized by stirring with a 20% solution of household bleach (1.1% sodium hypochlorite) for 30 min. employing several drops of Tween 20™ (per 100 mL sterilant) as a wetting agent. After three rinses with sterile water, immature embryos were aseptically excised from the arils and were plated horizontally onto the medium shown in Table 3. Cultures were incubated at 22° C. in the dark for four weeks. At the end of this time, the explants were transferred to fresh medium by simply moving the cultures to a new location on the original petri dish. After two additional weeks (total time=six weeks), the cultures were scored for the initiation of embryogenic tissue. Embryogenic tissue exhibited the translucent to white, mucilaginous phenotype characteristic of embryogenic conifer tissue.

Most often, embryogenic tissue originated in the cotyledon or hypocotyl region of the immature embryo explant. Embryogenic tissue was teased away from the original explant with a forceps and could thereafter be maintained as a purely embryogenic tissue culture on the same medium and under the same conditions described for initiation. Embryogenic tissue was serially maintained by transfer to fresh medium every three weeks.

The frequency of initiation of embryogenic tissue from immature Taxus embryos is illustrated for one particular collection (Corvalis, Oreg.) of immature *Taxus brevifolia* seed (see Table 4). Embryos that were just at the stage of cotyledon formation gave rise to embryogenic callus at a higher frequency than younger embryos that had not yet developed to the cotyledonary stage (see FIG. 1). The inclusion of casein hydrolysate (500 mg/L) in the medium afforded not only a higher initiation frequency from cotyledonary stage embryos but also made the initiation of embryogenic tissue from younger embryos possible.

The frequency of initiation of embryonic tissue from cultures other than *T. brevifolia* is shown in FIG. 3. These include *T. baccata*, *T. x media* and *T. cuspidata*.

Figure 5:
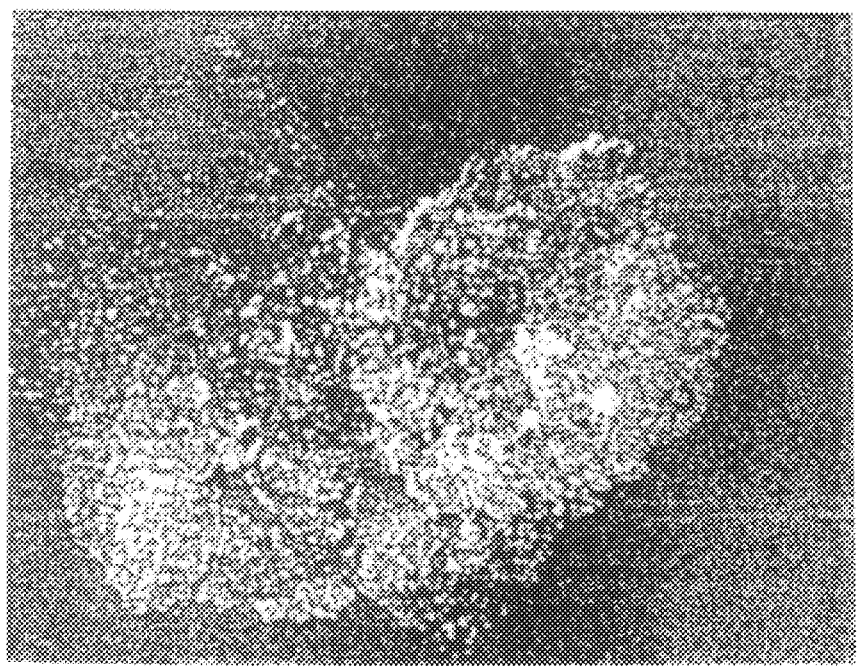
FIG. 5 shows a picture of a callus cell culture, *Taxus baccata* cv. 'Rependens' (cell line "A1"), grown on BLCG medium containing 2 mg/L 2,4-D and 1 mg/L BA (15×).

The embryogenic tissue employed in the method of the present invention is distinctly different from callus cell culture. For example, FIG. 5 shows a picture of a callus cell culture, *Taxus baccata* cv. 'Repends' (cell line "A1"), grown on BLCG medium containing 2 mg/L 2,4-D and 1 mg/L BA (15×). The amorphous appearance of the cells suggests a lack of organization.

Figure 6:
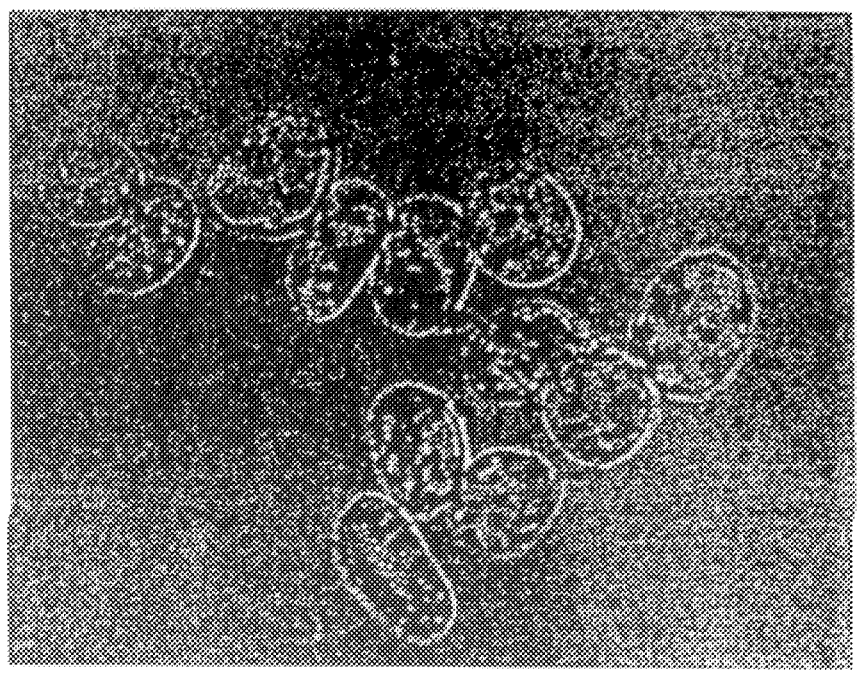
FIG. 6 shows a squash of cells taken from the culture shown in FIG. 5, at 250×.

FIG. 6 shows a squash of cells taken from the culture shown in FIG. 5 (250×). The lack of connection between the cells indicates that cells grown in callus culture grow independently from each other and are not organized into a tissue.

Figure 7:
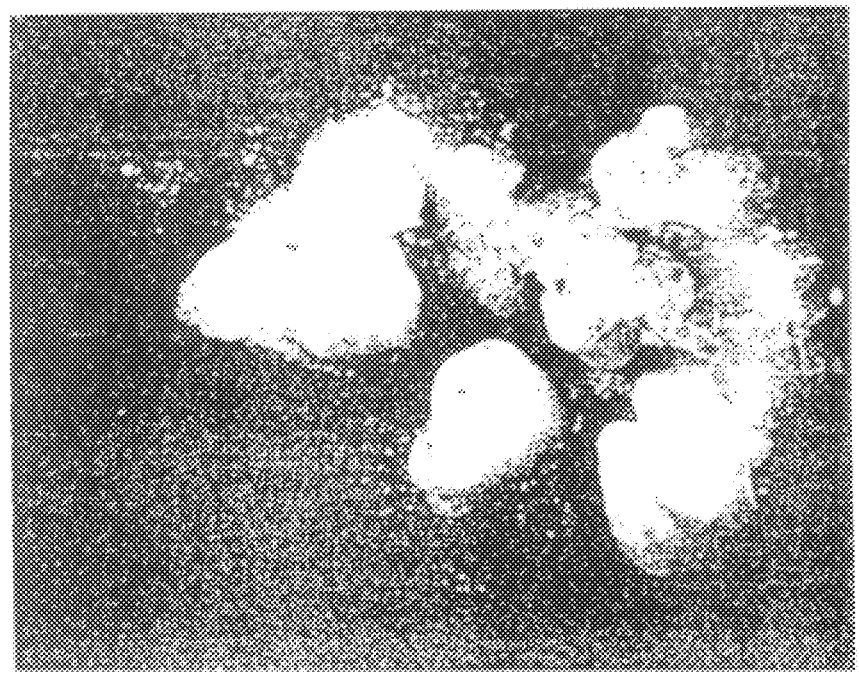
FIG. 7 shows a picture of an embryogenic tissue culture of *Taxus baccata* cv. 'Rependens' (cell line "A1"), grown on identical media as the callus cell culture of FIG. 5.

In contrast, embryogenic tissue culture of *Taxus baccata* cv. 'Repends' (cell line "A1"), grown on identical media as the callus cell culture of FIG. 5 shows the presence of organized structures (embryoids and somatic embryos) as indicated by the smooth, shiny, white structures of irregular shape (FIG. 7, 15×). Also, the absence of the amorphous callus material and the distinctly different appearance from callus cultures shown in FIG. 5 are notable. The culture depicted in FIG. 7 and the culture depicted in FIG. 5 are genetically identical, are the same chronological age, and are cultured on identical media. These results suggest that once an embryogenic state is reached, the tissue can be maintained independently from a callus state. The embryogenic tissue is not produced from callus tissue by manipulating the media, growth regulators or genotype.

Figure 8:
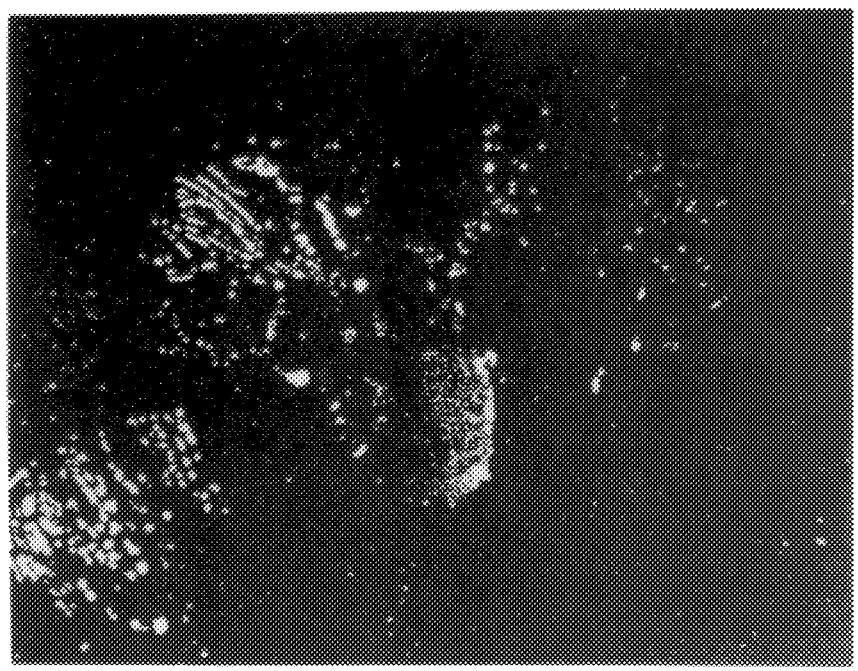
FIG. 8 shows a close-up photograph of somatic embryos from culture shown in FIG. 7, at 50×.

A close-up photograph of somatic embryos from culture is shown in FIG. 8 (50×). These embryos are less developed than those shown in FIG. 7. The dense apical "head" (or embryonal end) and the "tail" (suspensor region) composed of long, narrow cells are notable. These embryos are analogous to what would be found in a developing Taxus seed (i.e., zygotic embryos) about 1 month after fertilization.

These results, depicted in FIGS. 5–8, demonstrate that embryogenic tissue is distinct from callus culture.

Extraction and Determination of Taxane-Ring Containing Alkaloids from Embryogenic Tissue Taxol was analyzed in embryogenic tissue by a modification (M. Boyd, *Personal Communication* (August 1991)) of the published procedure (Witherup, K. M. et al., *J. Liq. Chromotgr.* 12:2117–2132, (1989)). Briefly, embryogenic Taxus tissue was homogenized in hexane in a Ten Breock tissue grinder. The hexane was discarded and the remaining plant tissue was extracted with 1:1 methylene chloride:methanol overnight at room temperature. The next day the mixture was filtered, and evaporated to dryness under a stream of nitrogen. The residue was dissolved in a minimal amount of methanol and was partitioned between 1:1 methylene chloride:water. The aqueous layer was discarded and the organic layer was evaporated to dryness. The residue was taken up in methanol and subjected to HPLC analysis.

HPLC analysis was performed using a phenyl bonded silica gel column operated under isocratic conditions employing a mobile phase consisting of (20:32:48) methanol:acetonitrile:50 mM aqueous ammonium sulfate buffer adjusted to pH 4.4 with acetic acid. The flow rate was 1 mL/mm and the effluent was monitored at 228 nm.

No taxol was observed being produced in embryogenic tissues containing proembryogenic masses and Stage 1 somatic embryos. However, several peaks were observed whose migration indicated that they are taxane-ring containing alkaloids other than taxol.

These results were confirmed using a polyclonal antibody-based indirect competitive inhibition enzyme immunoassay (CIEIA; Hawaii Biotechnology Group, Inc.).

TABLE 3

Composition of Media Used for Embryogenic Taxus Tissue Cultures

| Component | Concentration, mg/L |
|---|---|
| KNO$_3$ | 100 |
| MgSO$_4$.7 H$_2$O | 320 |
| KH$_2$PO$_4$ | 170 |
| CaCl$_2$.2 H$_2$O | 440 |
| KCl | 745 |
| KI | 0.83 |
| H$_3$BO$_3$ | 6.2 |
| MnSO$_4$.H$_2$O | 16.9 |
| ZnSO$_4$.7 H$_2$O | 8.6 |
| Na$_2$MoO$_4$.2 H$_2$O | 0.25 |
| CuSO$_4$.5 H$_2$O | 0.025 |
| CoCl$_2$.6 H$_2$O | 0.025 |
| FeSO$_4$.7 H$_2$O | 27.8 |
| Na$_2$ EDTA | 37.3 |
| Inositol | 100 |
| Nicotinic acid | 0.5 |
| Pyridoxine | 0.1 |
| Thiamine.HCl | 0.1 |
| Sucrose | 20,000 |
| Glutamine | 1,450 |
| Asparagine | 100 |
| 2, 4-D | 2 |
| Benzyl adenine | 1 |
| Bacto agar | 8,000 |
| pH = 5.8 | |

BLG 2/1 medium = above formulation
BLCG 2/1 medium = above formulation + 500 mg/L casein hydrolysate

TABLE 4

Initiation Frequency of Somatic Embryogenesis as a Function of Immature Embryo Development Stage In *Taxus Brevifolia* (6 weeks)

| Medium | Immature Embryo Stage (See below) | Embryos Cultured, No. | Embryogenic Callus, No. (%) |
|---|---|---|---|
| BLG 2/1 | 1–2 | 5 | 0 |
| | 3 | 10 | 0 |
| | 4–6 | 9 | 3 (33) |
| BLCG 2/1 | 1–2 | 6 | 0 |
| | 3 | 11 | 3 (27) |
| | 4–6 | 14 | 8 (57) |

Production of Taxol from Embryogenic Tissue Cultures of Taxus in Liquid Media

Taxol was not detected in embryogenic cultures of Taxus species that were maintained on agar-solidified, BLG-casein medium as just described. However, taxol was detected in the spent medium when embryogenic tissue was grown in liquid medium of the same composition in shake (110 rpm) flasks. Liquid cultures of embryogenic Taxus tissue were produced by dispersing masses of embryogenic tissue grown on agar-solidified medium in small volumes of liquid BLG-casein maintenance medium. After 1–2 months at 22° C. 110 rpm and an 8 h photoperiod under dim (80 foot-candles) fluorescent light, cultures consisting of small masses of tissue of uniform size were obtained. Until cultures of uniformly sized tissue masses were obtained, liquid media was replaced every 10–21 days by decanting spent medium and adding the same volume of fresh medium.

Once well-dispersed liquid cultures were obtained, taxol was produced in the following way. Cultures were inoculated into fresh medium by pipetting known volumes into fresh medium such that the inoculation density was 1 part mother culture to 10 parts fresh medium. Cultures were incubated with shaking under the conditions described above, and after 21 days the spent medium was collected. The spent medium was concentrated to dryness in vacuo and taxol was extracted and detected by HPLC (see FIG. 4).

Figure 4:
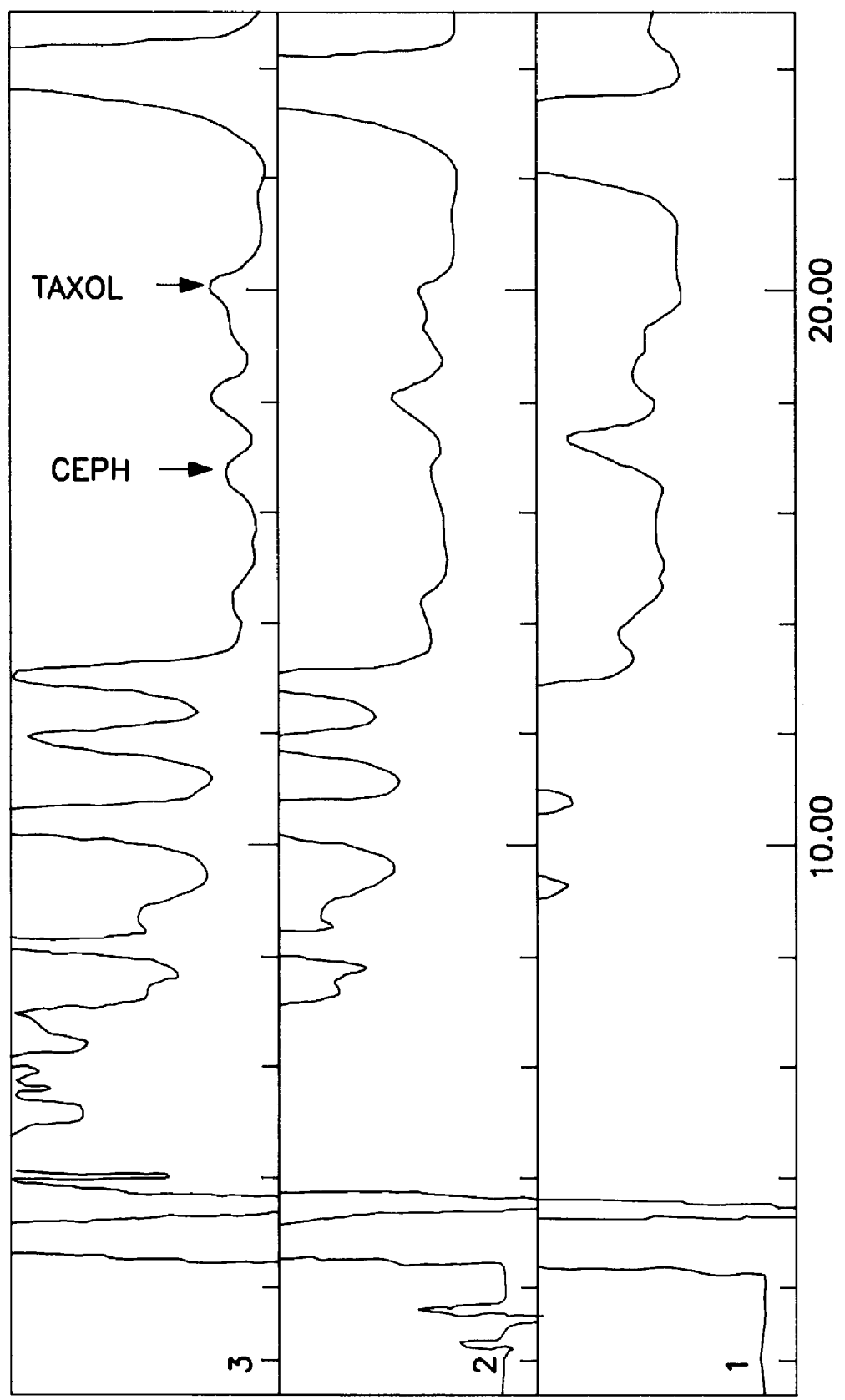
FIG. 4 shows a series of three HPLC traces, wherein trace 1 is an HPLC trace showing the separation of the components of an extract obtained by culture of *Taxus brevifolia* in liquid media. Trace 2 is an HPLC trace of a mixture of the *Taxus brevifolia* extract and a taxol standard. (3:1; see the peak at about 20.00 minutes). Trace 3 is an HPLC trace of a 1:1 mixture of the extract and taxol standard.

As shown in FIG. 4, trace 1, the Taxus *T. brevifolia* 'line H' extract contained a number of peaks which eluted at about the same place as a taxol standard. Trace 2 is an HPLC showing the separation of a 3:1 mixture of Taxus extract and taxol standard. It can be seen that the shoulder which eluted just before 20.00 minutes has increased in size. When a 1:1 mixture of Taxus extract and taxol standard were separated, this shoulder increased further, thus confirming the presence of taxol. Also evident are other taxane-ring containing compounds such as cephalomannine.

Verification of Production of Taxane Ring-Containing Compounds by Taxus Embryogenic Tissue ELISA analysis for taxane ring-containing compounds was performed on a number of samples of cells and spent media from suspension cultures described in the previous section entitled: Production of Taxol from Embryogenic Tissue Cultures of Taxus in Liquid Media. Taxanes were extracted from the cell biomass in the following way: cells were collected by filtration and were dried overnight in an oven at 60° C. After noting the mass of the dried cells, the cells were ground to a fine powder with a mortar and pestle. Methanol was added (5 ml/gm powdered cells), and the mixture was allowed to incubate at room temperature overnight. The next day, these cells were filtered and the filtrate was subjected to ELISA analysis for taxanes according to the procedure provided by the Hawaii Biotechnology Group, Inc., "Immunoassay System for the Quantitative Detection of Taxanes in Biological Matrices," (HBG, Inc. Product Brochure). Methanolic extracts were diluted 1:5 in water prior to ELISA analysis.

The results of the ELISA analysis are shown in Tables 5 and 6 as follows:

TABLE 5

Taxane Content of Taxus spp. Embryogenic Tissue Cultures

| Cell Line | Culture Type | Taxane ng/gm (o.d.) or mL |
|---|---|---|
| *T. brevifolia* (line L) | agar-solidified | 1,353 |
| *T. brevifolia* (line msgo C) | agar-solidified | N.D. |
| *T. brevifolia* (line O) | agar-solidified | N.D. |
| *T. brevifolia* (line M) | agar-solidified | 307 |
| *T. brevifolia* (line 92-3-5) | agar-solidified | N.D. |
| *T. brevifolia* (line 92-3-1) | agar-solidified | N.D. |
| *T. x media* (line B) | agar-solidified | N.D. |
| *T. x media* cv. 'Hicksii' (line 1A) | agar-solidified | N.D. |
| *T. baccata* cv. 'Repdendens' (line A1) | agar-solidified | 416 |
| *T. brevifolia* (line H) | suspension culture | |
| a)[1] control | cell fraction | 323 |
| b)[2] +350 μM Cu$^{+3}$ | cell fraction | 188 |

N.D. = none detected
[1] Sample contained no copper
[2] Sample treated with copper ion in an attempt to induce an increased level of taxol production.
[3] +350 μM Cu$^{++}$ indicates that copper ion was added to a concentration of 350 μM.

As can be seen in Table 5, Taxus embryogenic tissue cultures contain taxane. This ELISA data confirms the results shown in FIG. 4 which indicates (chromatographically) that taxane ring-containing compounds are produced by embryogenic tissue.

TABLE 6

Taxane Content of Cells and Spent Media from Taxus Embryogenic Suspension Cultures

| Species/Line | Fraction | Age, weeks | Final Cell Density, gm (d.b.)/L | Taxane, ng/gm or ng/L |
|---|---|---|---|---|
| T.brevifolia 'H' | Cells | 16 | 2.6 | 24 |
|  | Media | — | — | 12 |
| T. x media 'C' | Cells | 15 | 2.8 | 0 |
| 'Flushing' | Media | — | — | 23 |

The ELISA data reported in Tables 5 and 6 was obtained as described above by the procedure developed by the Hawaii Biotechnology Group, Inc. The data are the average of duplicate determinations in all cases. In addition, control samples (not containing taxol) as well as taxol standards were used to prepare a standard curve according to the section entitled "Quality Control" in the HBG, Inc. Product Brochure. Thus, the results convincingly prove that taxol was in fact produced in Taxus embryogenic tissue.

Example 2

Increasing Taxol Production from Embryogenic Taxus Cultures by the Production of Precocious Neomorphic Embryoids (PNE)

Embryogenic *Taxus cultures of T. x. media cv.* 'Hicksii' (cell line 92–3–1) and *T. baccata* cv. 'Repemdens' (cell line A1) were maintained in the dark at 24 ° C on either: (1) WPM media containing 0.02 or 0.5 mg/L TDZ or (2) BLCG media containing 0.5 mg/L B.A. All media was supplemented with 3% sucrose, 500 mg/L casein hydrolysate and was solidified with 0.25% gelrite. For taxol production, embryo development and precocious germination was induced by transfer of embryogenic tissue to media lacking plant growth regulators (PGRs). Specific formulations tested were: (1) SH (Schenk and Hildebrandt) media; (2) GD (Gresshof and Doy) media containing 0.5% activated charcoal and (3) half-strength WPM containing 0.5% activated charcoal. After four weeks, taxol concentration of the tissue was determined by ELISA using a taxol-specific antibody (Hawaii Biotechnology Group).

The taxol concentration of the tissue subjected to an embryo development protocol is shown in Table 7. The lowest concentrations of taxol were found in embryogenic tissue grown under proliferative conditions (media containing TDZ). Under proliferative conditions, embryo development rarely proceeds beyond the most rudimentary level, and taxol content, though low, is measurable. Upon transfer of embryogenic tissue to media lacking growth regulators, precocious germination begins immediately. After four weeks on SH media without PGRs the taxol content had increased 426% and 814% in the *T. x media* cv. 'Hicksii' and *T. baccata* cv. 'Repemdens' cell lines, respectively. The last entry in Table 7 describes growth condition of PNEs producing highest levels of taxol concentration in those experiments summarized in Table 7. It should also be noted that said entry in Table 7 describes PNEs which were the greenest of all PNEs in Table 7. Hence, it demonstrates the correlation between production of chlorophyll (greening) and production of biological products (here, taxol).

In the *T. baccata* 'Repemdens' cell line, precocious germination proceeded to an advanced degree on half strength WPM containing charcoal, as indicated by the formation of cotyledons and a marked greening of the tissue. The taxol content of this tissue was 18,274 ng taxol/gm or 0.0018% on a dry weight basis. This concentration is similar to that reported for some callus culture cell lines (Fett-Neto et al., *Bio/Technology* 10:1572–1575 (1992)), and is approaching the concentration typically found in needle or stem tissue of Taxus species (approximately 0.01%).

TABLE 7

Taxol Concentration of the Tissue Subjected to an Embryo Development Protocol

| Cell Line | Proliferation Media (see below) | Differentiation Media | Response | [Taxol], ng/gm d.w. |
|---|---|---|---|---|
| 92-3-1 | 1 | None (Control) | Proliferation | 57 |
|  | 2 | 3 | PNE Formation | 300 |
| A1 | 1 | None (Control) | Proliferation | 50 |
|  | 1 | 3 | PNE Formation | 1,202 |
|  | 2 | 3 | PNE Formation | 457 |
|  | 2 | 4 | PNE Formation | 1,886 |
|  | 5 | 6 | PNE Formation | 18,274 |

1 = WPM with 0.02 mg/L TDZ
2 = WPM with 0.5 mg/L TDZ
3 = SH with no PGRs
4 = GD with 0.5% activated charcoal and no PGRs
5 = BLCG with 0.5 mg/L BA
6 = Half-strength WPM with 0.5% activated charcoal and no PGRs Having fully described this invention, it will be understood by those skill in art that it can be performed within any wide range of equivalent modes of operation as well as other parameters without affecting the scope of the invention or any embodiment thereof.

All patents and publications cited in the present specification are incorporated by reference herein in their entirety.

What is claimed is:

1. An isolated Taxus precocious neomorphic embryoid.

2. A tissue culture as which comprises Taxus precocious neomorphic embryoids.

3. A method of producing a taxane-ring containing compound which comprises making Taxus precocious neomorphic embryoids and isolating the taxane=ring containing compound therefrom.

4. A method of obtaining a precocious neomorphic embryoid of a plant species of interest which comprises inducing maturation of embryos in a growth medium in which plant growth regulators have been removed or their amounts have been reduced, in comparison with media ordinarily used to culture embryos of the plant species of interest, until early to mid-stage development is reached; wherein n comparison with media ordinarily used to culture embryos of the plant species of interest, a high amount of reduced organic nitrogen is present in the medium to generate said precocious neomorphic embryoid.

5. A method of obtaining a Taxus precocious neomorphic embryoid which comprises inducing maturation of embryos in a growth medium in which plant growth regulators have been removed or their amounts have been reduced, in comparison with media ordinarily used to culture Taxus embryos until early to mid-stage development is reached; wherein in comparison with media ordinarily used to culture Taxus embryos, a high amount of reduced organic nitrogen is present in the medium to generate said Taxus precocious neomorphic embryoid.

6. An isolated Taxus precocious neomorphic embryoid in a medium in which it can be maintained.

7. A method of obtaining a Taxus precocious neomorphic embryoid which comprises (a) inducing maturation of embryos in a growth medium in which plant growth regulators have been removed or their amounts have been reduced, in comparison with media ordinarily used to culture Taxus embryos and (b) harvesting precocious neomorphic embryoids from the medium.

8. The method of claim 7 which further comprises the step of isolating a taxane-ring containing compound from the harvested precocious neomorphic embryoids.

* * * * *